(12) United States Patent
Hadj Henni et al.

(10) Patent No.: US 9,494,475 B2
(45) Date of Patent: Nov. 15, 2016

(54) APPARATUS, SYSTEM AND METHOD FOR DYNAMICALLY MEASURING MATERIAL VISCOELASTICITY USING SHEAR WAVE INDUCED RESONANCE

(75) Inventors: Anis Redha Hadj Henni, Montreal (CA); Cedric Rene Schmitt, Montreal (CA)

(73) Assignee: VAL-CHUM, LIMITED PARTNERSHIP, Montreal (CA)

( * ) Notice: Subject to any disclaimer, the term of this patent is extended or adjusted under 35 U.S.C. 154(b) by 625 days.

(21) Appl. No.: 13/825,340

(22) PCT Filed: Sep. 26, 2011

(86) PCT No.: PCT/CA2011/050600
§ 371 (c)(1),
(2), (4) Date: Mar. 21, 2013

(87) PCT Pub. No.: WO2012/037695
PCT Pub. Date: Mar. 29, 2012

(65) Prior Publication Data
US 2013/0174666 A1    Jul. 11, 2013

Related U.S. Application Data

(60) Provisional application No. 61/386,537, filed on Sep. 26, 2010.

(51) Int. Cl.
*G01L 1/24* (2006.01)
*G01N 11/16* (2006.01)
*G01N 3/06* (2006.01)

(52) U.S. Cl.
CPC ............... *G01L 1/24* (2013.01); *G01N 11/16* (2013.01); *G01N 3/068* (2013.01); *G01N 2203/0094* (2013.01)

(58) Field of Classification Search
None
See application file for complete search history.

(56) References Cited

U.S. PATENT DOCUMENTS

| 3,901,074 A | 8/1975 | Douglas |
| 5,099,848 A | 3/1992 | Parker et al. |

(Continued)

FOREIGN PATENT DOCUMENTS

| CA | 2732334 A1 | 2/2010 |
| EP | 1141696 | 10/2001 |
| JP | 2000-187024 A | 7/2000 |

OTHER PUBLICATIONS

Souchon, R., Salomir, R., Beuf, O., Milot, L., Grenier, D., Lyonnet, D., Chapelon, J.-Y. and Rouvière, O. (2008), Transient MR elastography (t-MRE) using ultrasound radiation force: Theory, safety, and initial experiments in vitro. Magn Reson Med, 60: 871-881. doi: 10.1002/mrm.21718.*

(Continued)

*Primary Examiner* — Hezron E Williams
*Assistant Examiner* — Mark A Shabman
(74) *Attorney, Agent, or Firm* — Price Heneveld LLP

(57) ABSTRACT

A system for dynamically measuring viscoelasticity of material samples using shear wave induced resonance, the system comprising: i) an apparatus comprising a vibration source; a vibration detector; a processor, and a user interface, for example to select a sample holder configuration, and ii) a rigid sample holder connectable to the vibration source, wherein the vibration source generates shear waves that induce vibrations and the resonance of a sample through the holder, the vibration sensor measuring the sample vibrations and resonance, and the processor determining the viscoelasticity of the sample from the vibrations or resonances and from the selected sample holder configuration. Multiple measurement modalities using the system to study materials viscoelasticity as function of time parameters; temperature parameters; strain parameters; repetition parameters and mapping parameters.

29 Claims, 19 Drawing Sheets

(56) References Cited

U.S. PATENT DOCUMENTS

| | | | | |
|---|---|---|---|---|
| 5,196,343 | A | * | 3/1993 | Zerhouni .............. G01N 29/30 252/408.1 |
| 5,592,085 | A | | 1/1997 | Ehman |
| 6,037,774 | A | | 3/2000 | Felmlee et al. |
| 6,386,045 | B1 | | 5/2002 | Nakamura et al. |
| 2003/0193336 | A1 | * | 10/2003 | Ehman ............... G01R 33/4833 324/309 |
| 2005/0004463 | A1 | | 1/2005 | Chen et al. |
| 2005/0054930 | A1 | * | 3/2005 | Rickets .................. A61B 5/416 600/453 |
| 2009/0105588 | A1 | * | 4/2009 | Emelianov ........... A61B 5/4869 600/438 |
| 2010/0138163 | A1 | | 6/2010 | Gallippi et al. |
| 2010/0154567 | A1 | | 6/2010 | Menard |
| 2011/0130660 | A1 | * | 6/2011 | Cloutier .............. A61B 5/0048 600/438 |

OTHER PUBLICATIONS

Chen Shigao et al., 'Quantifying elasticity and viscosity from measurement of shear wave speed dispersion', the Journal of the Acoustical Society of America, vol. 115 No. 6 Jun. 1, 2004, pp. 2781-2785.

Cho Seung et al., 'High-frenquency torsional modal testing of a long cylinder by magnetostriction', Applied physics letters, AIP, vol. 91 No. 7, Aug. 14, 2007 pp. 71908-1 to 71908-3.

Hsieh C P et al., 'Novel technique of NDE in ceramic bearing balls', Dec. 8, 1991, pp. 891-894.

Parker Kevin et al., 'A unified view of imaging the elastic properties of tissue', the Journal of the Acoustical Society of America, vol. 117 No. 5 May 1, 2005, pp. 2705-2712.

PCTCA2011050600 international preliminary report.

PCTCA2011050600 international search report with claims 1-29.

Schmitt C et al., '11C-5 Characterization of Time-Varying Mechanical Viscoelastic Parameters of Mimicking Deep Vein Thrombi with 2D Dynamic Elastography', Ultrasonics Symposium, 2007 IEEE, Oct. 1, 2007 pp. 1009-1012.

Hurley D C et al., "Atomic force acoustic microscopy methods to determine thin-film elastic properties", Journal of Applied Physics, American Institute of Physics, US, vol. 94, No. 4, Aug. 15, 2003, pp. 2347-2354, XP012059961.

The Hague; Supplementary European Search Report, May 23, 2016.

* cited by examiner

Figure 1-A
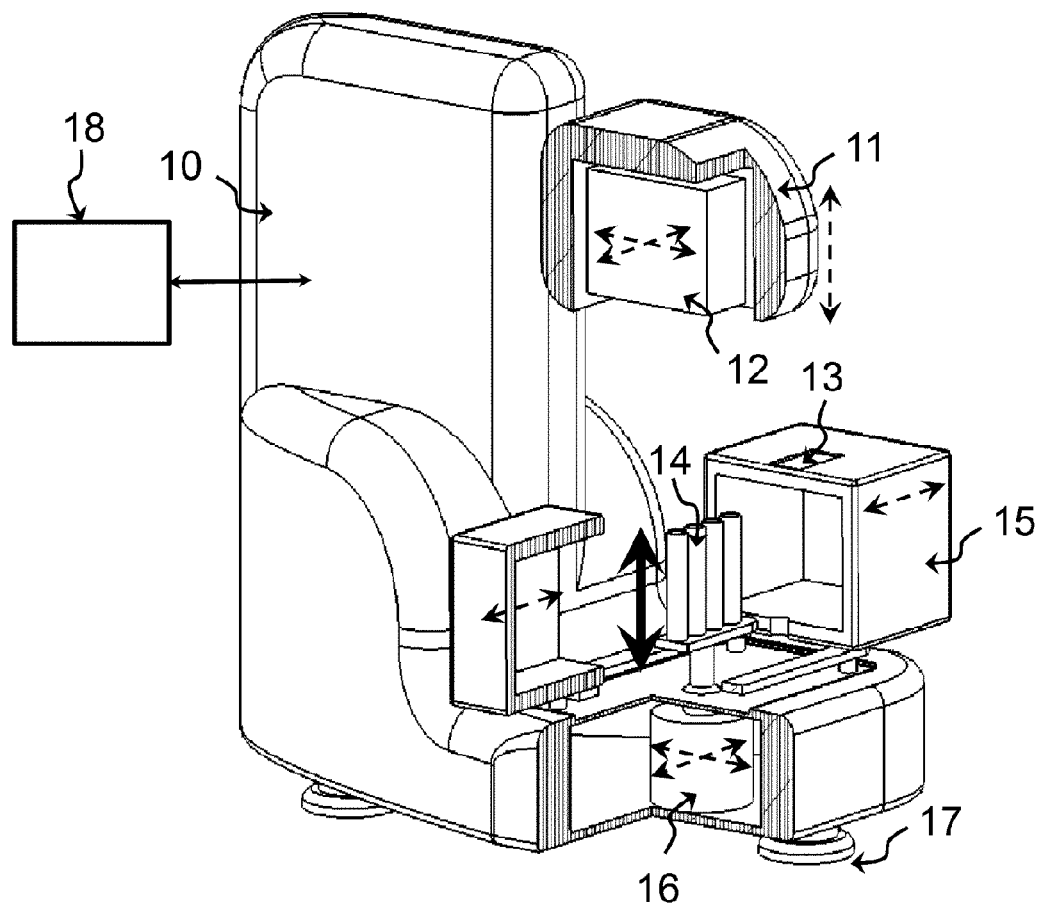

Figure 1-B
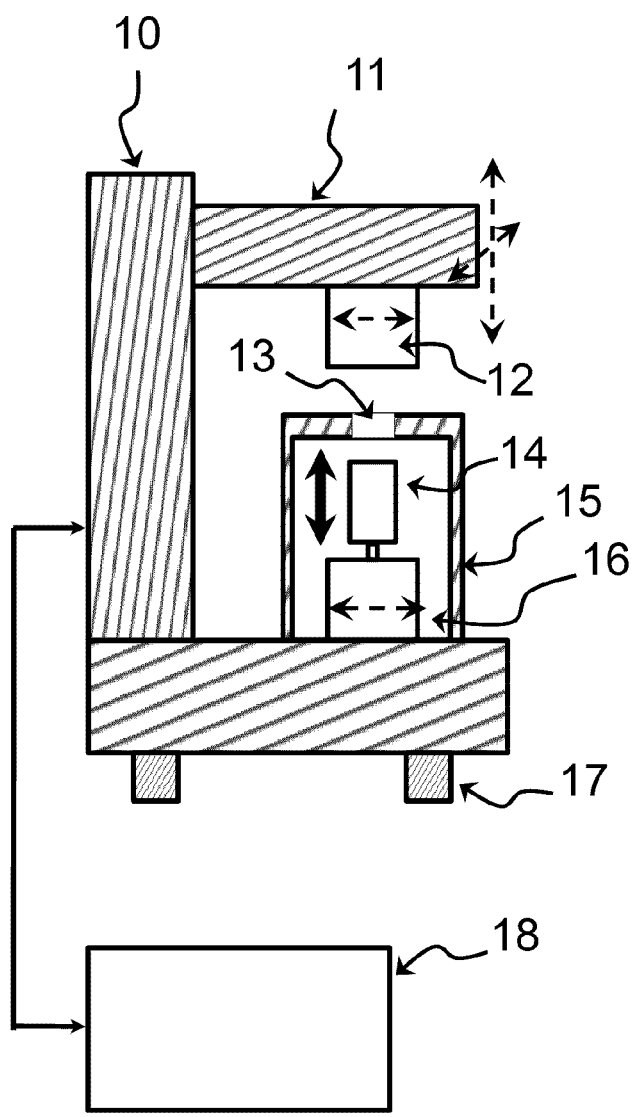

Figure 1-C
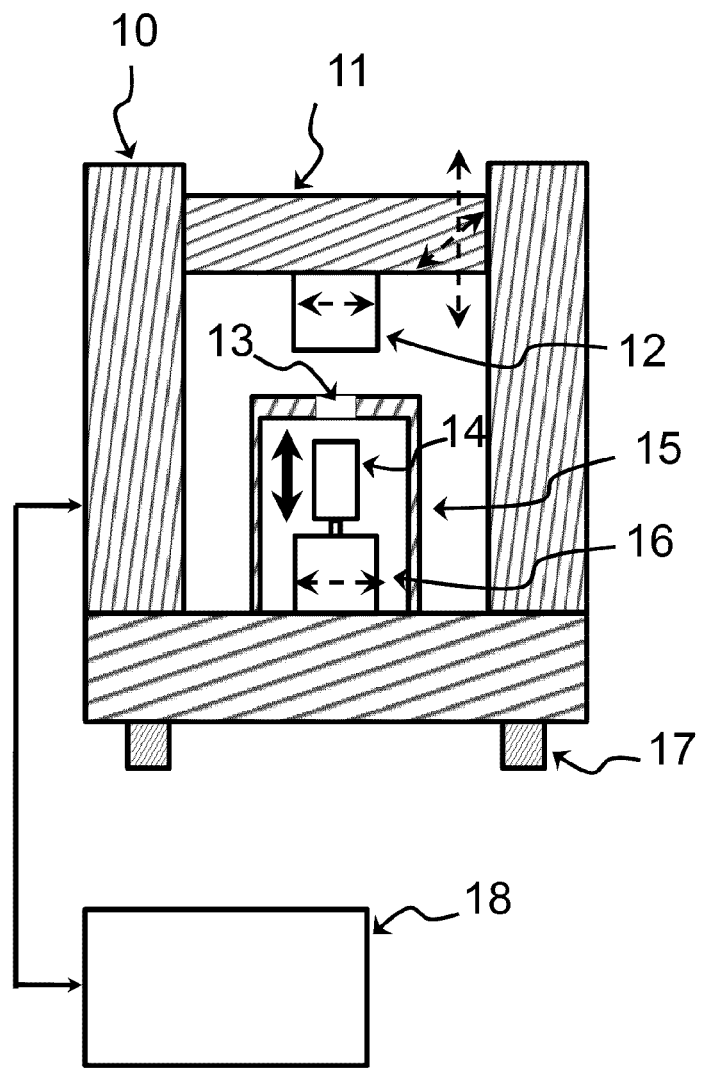

Figure 2-A
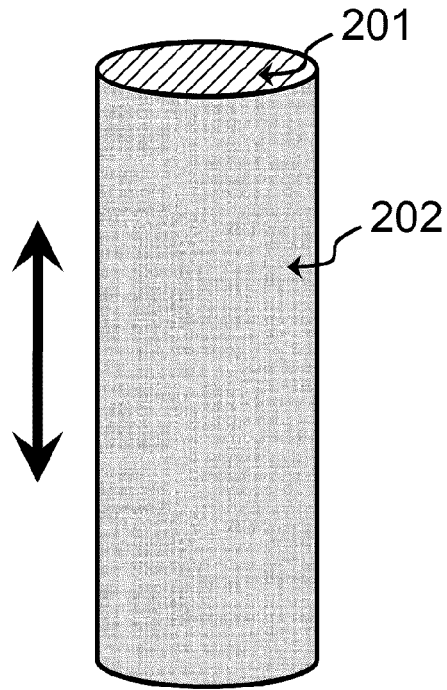
Figure 2-B
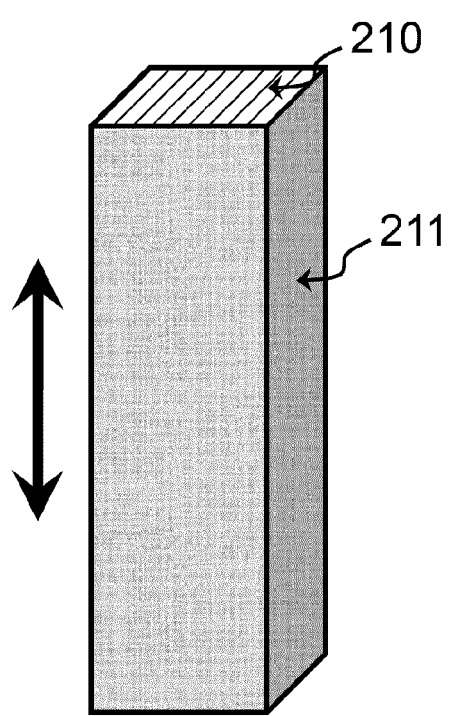

Figure 3-A
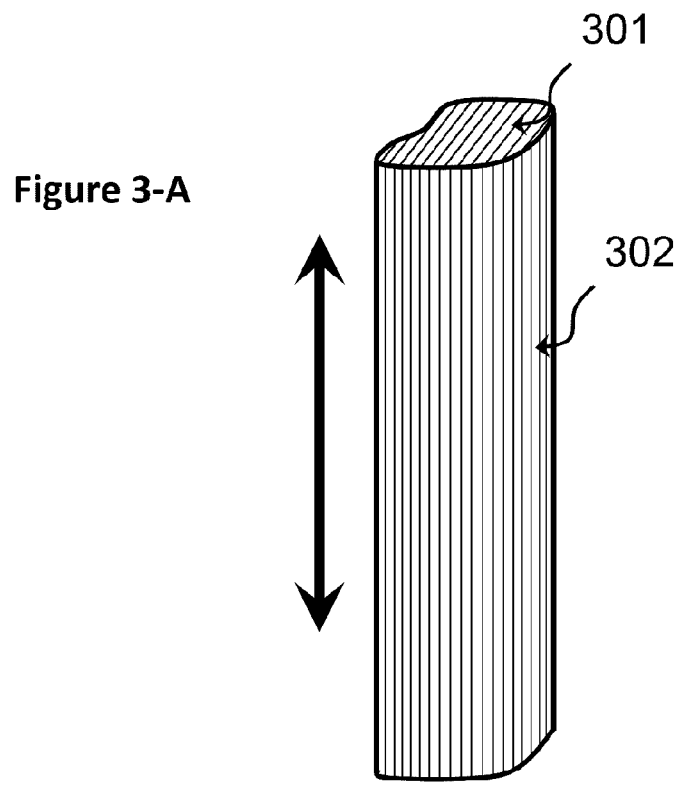
Figure 3-B
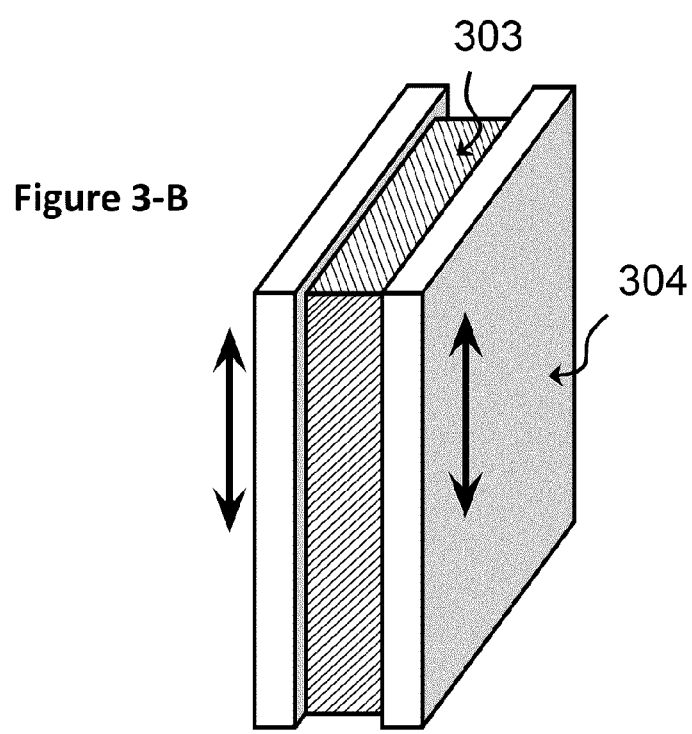

Figure 4-A (a)
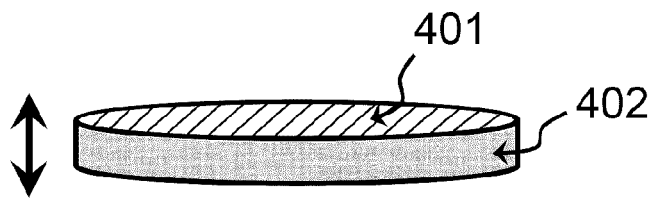
Figure 4-A (b)
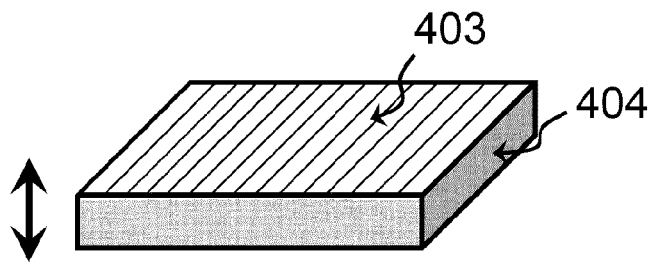
Figure 4-A (c)
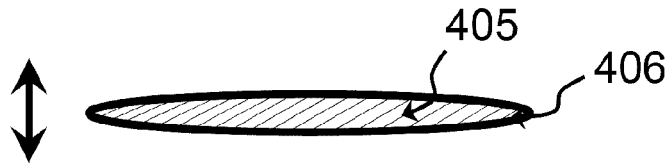
Figure 4-A (d)
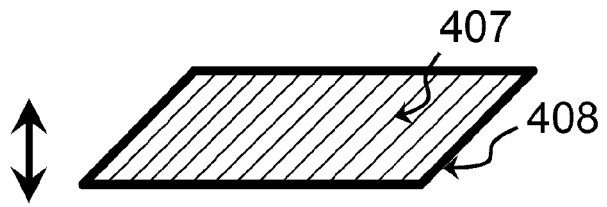

Figure 4-B
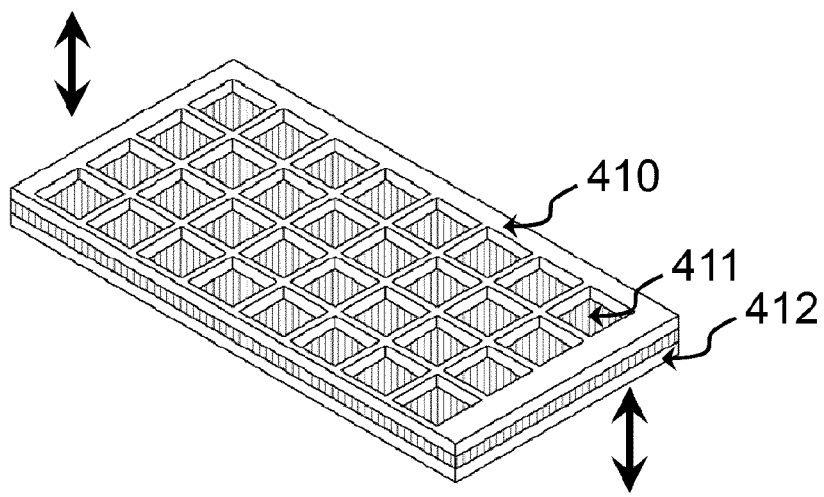
Figure 4-C
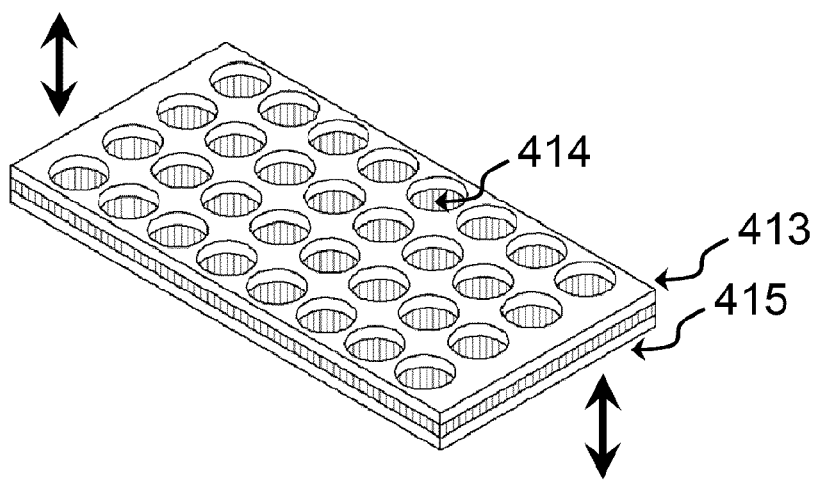

Figure 5-A (a)
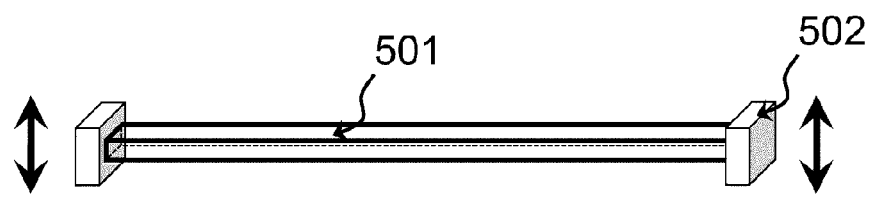
Figure 5-A (b)
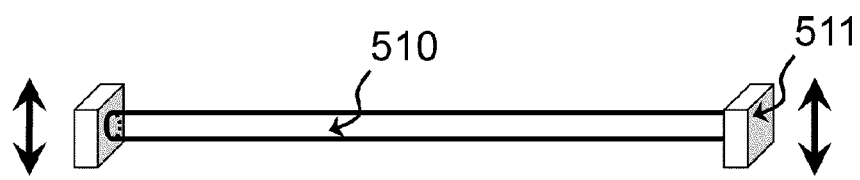

Figure 5-B (a) 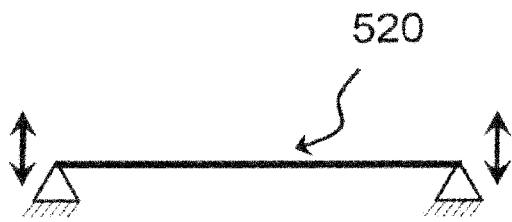
Figure 5-B (b) 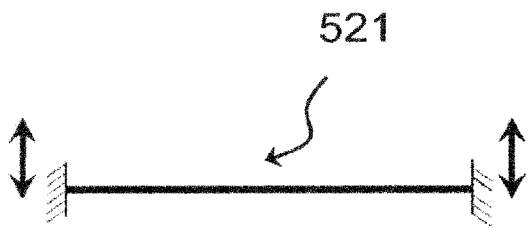
Figure 5-B (c) 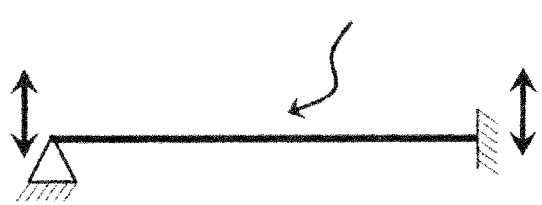
Figure 5-B (d) 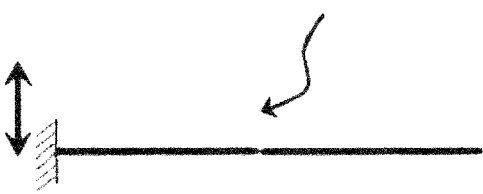

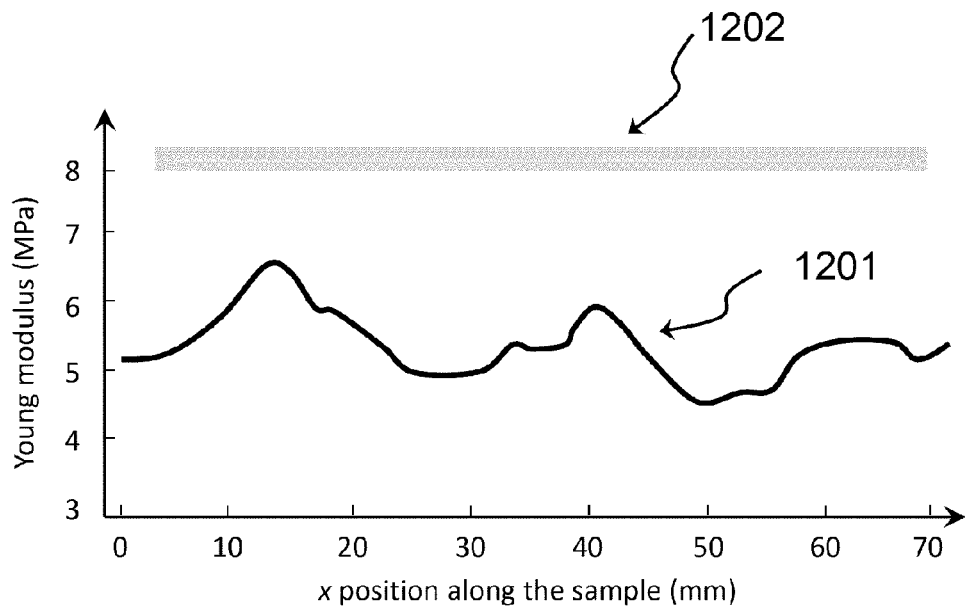
Figure 12
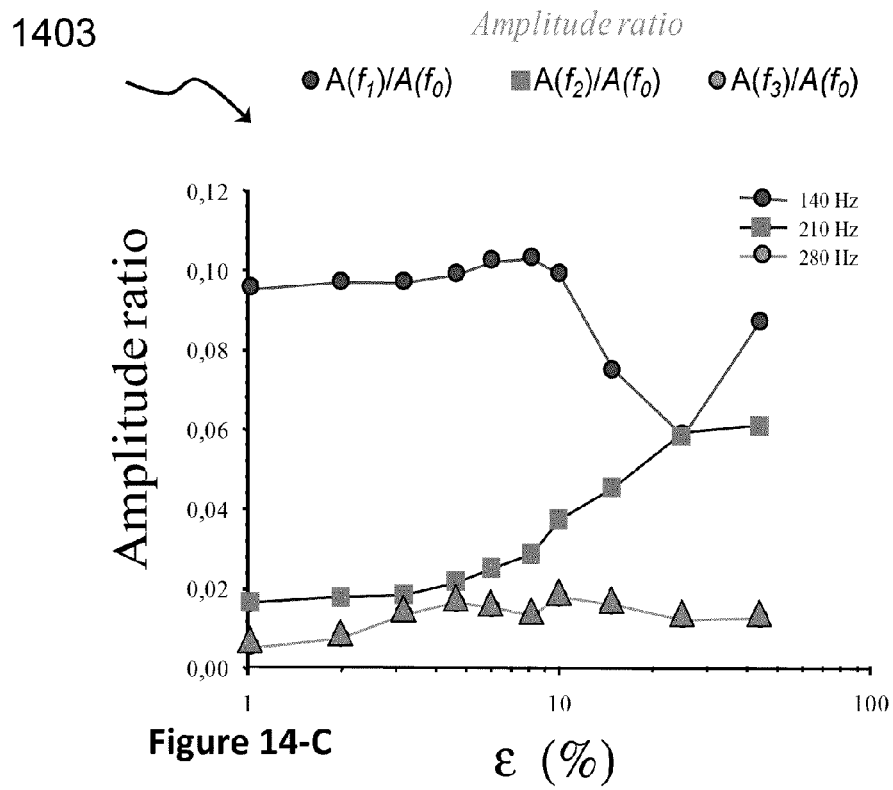
Figure 14-C

Figure 13-A
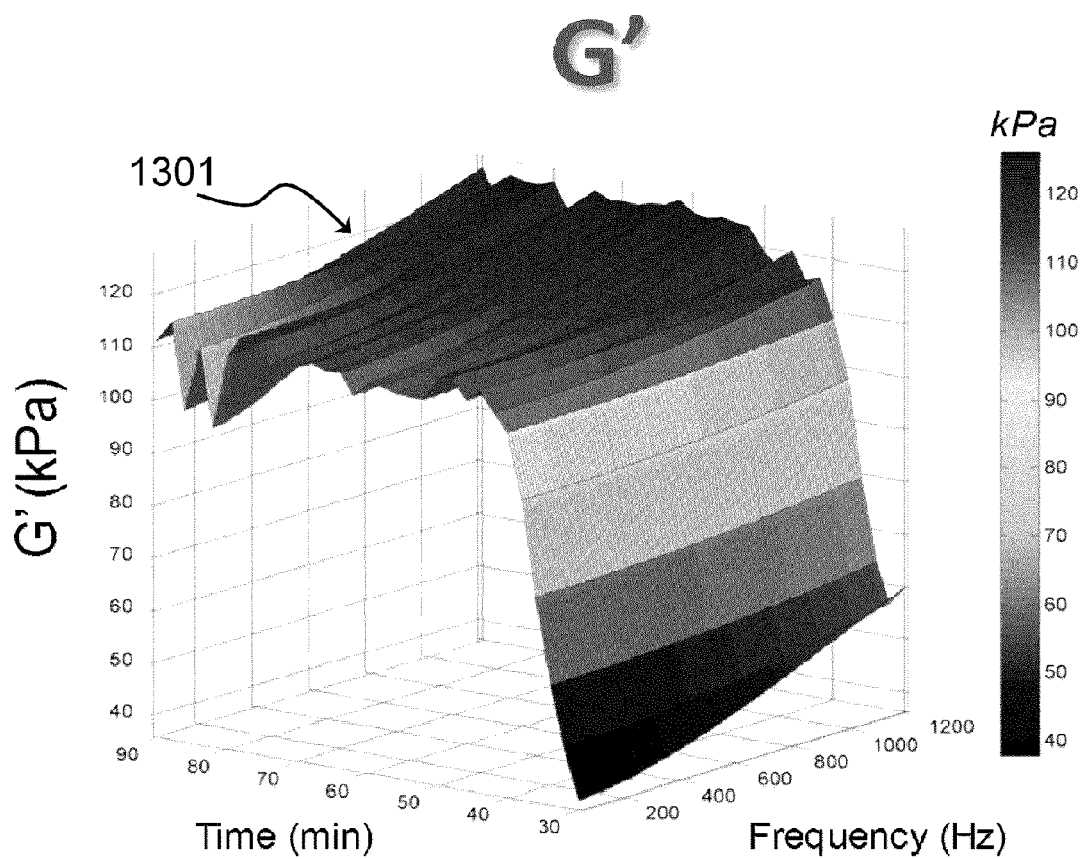

Figure 13-B
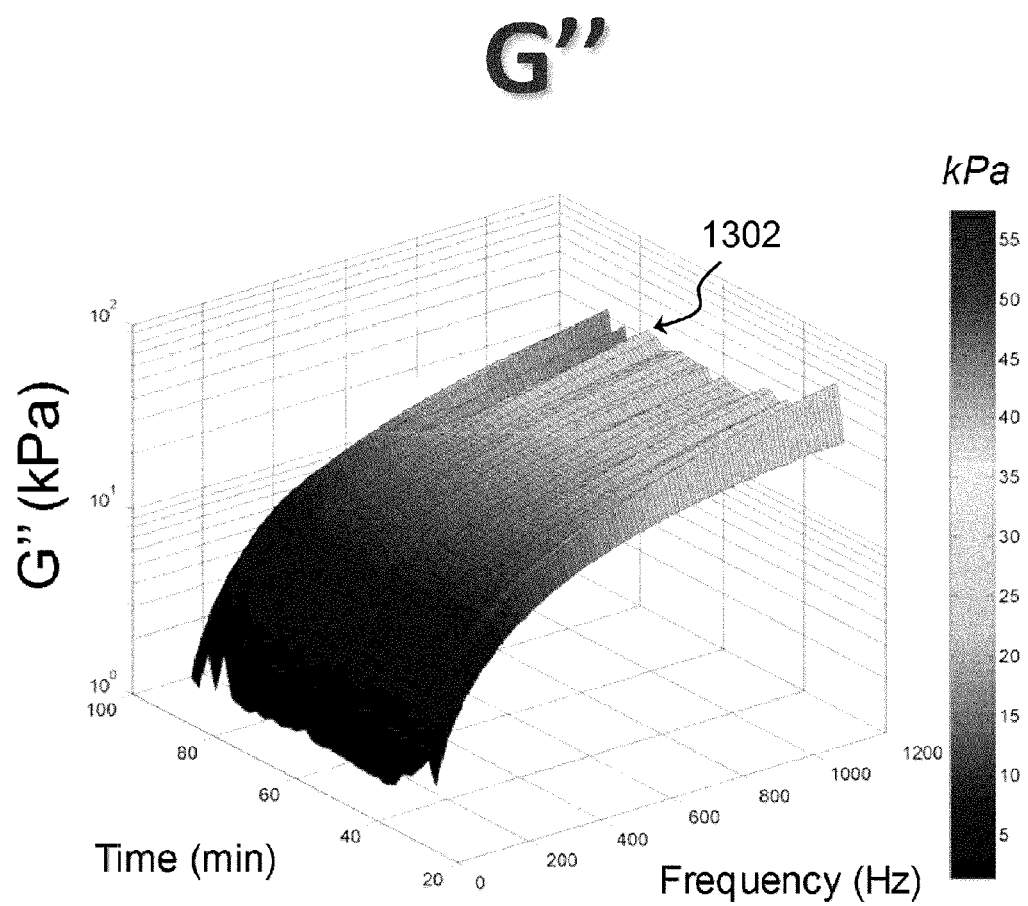

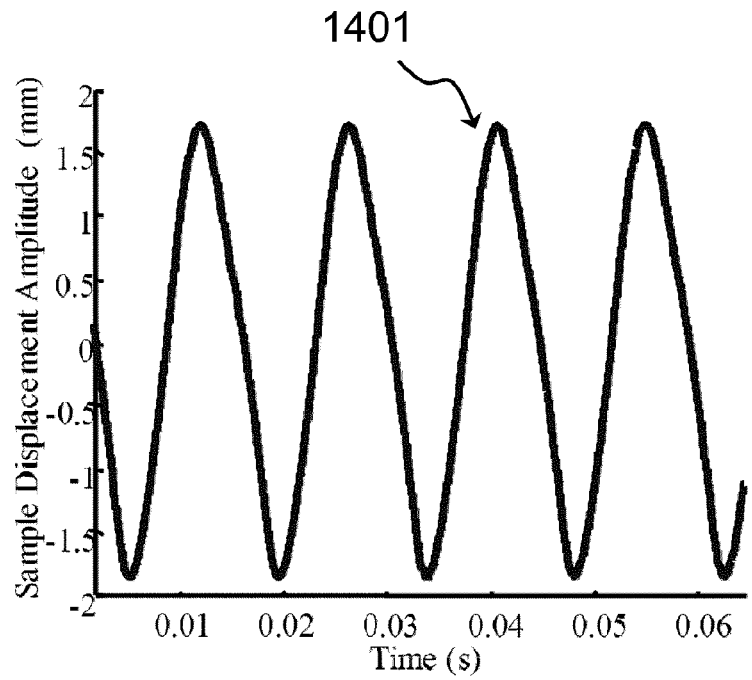
Figure 14-A
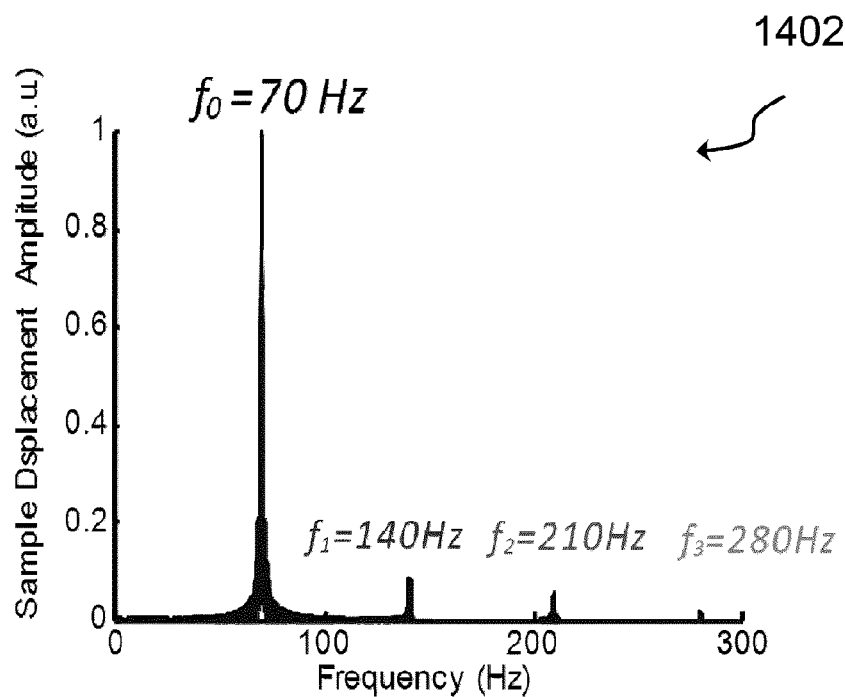
Figure 14-B

APPARATUS, SYSTEM AND METHOD FOR DYNAMICALLY MEASURING MATERIAL VISCOELASTICITY USING SHEAR WAVE INDUCED RESONANCE

This application claims priority of U.S. provisional patent application 61/386,537 filed Sep. 26, 2010.

FIELD

The present invention generally relates to an apparatus, a system and a method for dynamically measuring viscolelasticity of materials. More specifically, the invention relates to an apparatus and related material sample holding means and user selectable testing modalities to perform non-contact spectroscopic measurement of material elasticity and/or viscosity (i.e. viscoelasticity).

BACKGROUND

Mechanical characterization of materials has to contend with challenges such as non-destructive measurements (in the case of expensive or rare sample materials, or to allow the re-use of the same sample after mechanical characterisation), hyper-frequency viscoelastic characterization (wide-band frequency viscoelasticity, elasticity or viscosity), viscoelastic evaluation as function of temperature, fast measurements (important when mechanical parameters or environmental configuration change rapidly) and simplicity of use. Precise, accurate and fast measurement of viscoelastic spectroscopy as function of temperature is essential for the conception, the optimization, the quality control, and the safe and efficient use of material in real conditions.

For example, the seals, gaskets or o-rings installed in major parts of a jet fighter have to be in accordance with critical thermo-mechanical specifications since, during the takeoff and the flight, the material is subjected to a huge increase or decrease in temperature in a very short time and a significant vibration in a high frequency band. Another example is the rubber employed to build tires of airplanes for which they has to be optimally designed and tested to withstand significant compression, very fast temperature increase and wide-band high frequency vibration during plane landing. Another example, in the biomedical application, is the development of implantable synthetic heart tissues that have to mimic as closely as possible the mechanical properties of real human heart tissue. Since the heart is a moving and vibrating tissue, accurate knowledge of its viscoelasticity is a key point parameter that will have an important impact on it safety in real conditions (i.e. implanted in humans). Such measurement also has to be done non-destructively and contactless for quality control of biomaterials before implantation.

Various systems and methods have been contemplated in the prior art to measure viscoelastic properties of material samples. Rotational rheometers (RHE), Dynamic Mechanical Rheological Testing (DMRT), Dynamic Mechanical Analysis (DMA) of materials, indentation system (IS) are typical systems currently in use to that purpose.

RHE and DMRT instruments are based on the characterization of a disk-shaped sample sandwiched between two plates, the upper plate applying a shear strain to the tested sample and measuring in the same time the oscillatory shear stress. The DMA instruments are based on the compression of cylindrical or rectangular samples using a large rigid plate, the opposite plate being connected to a load sensor employed to measure the induced stress. In the case of IS, the sample is placed on a rigid plate connected to a load sensor and a small tip of different size and shape is used to indent, at different depth, the upper surface of the sample.

All the above-mentioned systems are mainly limited in performance by their relatively low test frequency range (typically below 200 Hz), the long measurement time (typically 30 min for a full frequency sweep), the restriction of sample size and shape (thin disk or slice usually difficult to prepare), the complex fixtures used to enable recording of the sample behaviour and the use of functional mechanical elements in contact with the tested sample (which results in the limitation to one sample measurement at a time and in the destruction of tested samples).

United-States patent application No 2010/012092 by Cloutier et al. discloses a system and method for detection, characterisation and imaging of a heterogeneity using shear wave induced resonance. In Cloutier et al, the viscoelastic sample is contained as a heterogeneity within a non-rigid, viscoelastic medium. This latter can be contained in a rigid container or simply in contact with it. In an embodiment, a system of particular interest is taught comprising a vibration source; a container for a sample, said container being connected to the vibration source; a vibration detector; and a processor, wherein the vibration source generates shear waves that induce vibrations and the resonance of the sample in said container, the vibration sensor measuring the sample vibrations and resonances and the processor determining the viscoelasticity of said sample from said resonances. However, the disclosure mainly aims at detecting and characterizing a heterogeneity in a body and provides very limited hints for investigating and developing possible applications in the field of materials testing.

Therefore, it is desired to overcome or reduce at least some of the above-described problems and limitations of the prior art.

SUMMARY

Nevertheless, shear wave induced resonance (SWIR) presents good potential for dynamically measuring the viscoelasticity of materials and samples of given (or known) geometry, using an apparatus to perform viscoelastic spectroscopy on material samples by generating and propagating shear waves therein. It has been demonstrated that the shear dynamical response of a material sample or structure can be used to measure its spectroscopic viscoelasticity. Also, the constructive superposition of shear waves in the material volume can induce stationary vibrations and particular resonances that depend on both geometry and viscoelastic (or rheological) properties of the material. Therefore, shear wave resonance induction in a finite and geometrically known sample or structure could serve to measure the spectroscopic viscoelasticity. The measured free vibration spectrum of a material sample depends on the material viscoelasticity and contains the viscoelastic spectroscopic material signature.

Viscoelastic spectroscopic measurements may be performed over a wide frequency range going from 1 Hertz to more than 10 000 Hertz, which enables dynamic measurement of a broad range of materials with very different physico-chemical and mechanical characteristics.

The present invention describes an apparatus allowing to measure very quickly (at least 900 times faster than other technology), fully automatically, and contactless the viscoelasticity, the elasticity or the viscosity of samples in a frequency range at least 30 times than previous systems. The tested material is partially confined in a container and can be of a large variety of shape and size according to the information needed and the nature of the material.

A major advantage of that technology is the method of shear wave generation into the sample material or structure. Shear waves for resonance induction can be transmitted to the material using a container confining the material sample. Furthermore, induced mechanical resonances or shear dynamical responses can be measured without physical contact with the sample, by means such as lasers, microphones, air-coupled ultrasound, eddy current or any non-contact measurement technique known in the art. However, using the technology to measure viscoelastic properties of different materials having different shapes and mechanical properties poses the challenging goal of providing appropriate sample confinement or holding techniques and adapting processing of the measured spectral data to the type of sample holding means being used.

It would therefore be desirable to provide a system and method which enable testing of a wide variety of material types being available as samples with different geometries and adapting data processing accordingly to ensure reliable measurement in any condition. It would further be desirable to enable testing of material samples in different environmental conditions, in order to characterise viscoelastic properties at different ambient temperatures or pressures for example. In addition, it would further be desirable to perform measurements following new modalities allowing, for example, the mapping of viscoelasticity distribution over a material sample or structure.

The terms "means" and "by the means of", when used in the present description, are intended to mean "device or mechanism" and "using", respectively.

The terms, "shear wave induced resonance" and "vibration induced (or inducing) resonance" as used herein are intended to be understood in the sense of displacement amplifications, in comparison to the excitation, when a material sample is subjected to vibrations by the system sample holder-vibration source of the instrument. Depending on the viscoelastic properties of the material, resonance frequencies can or cannot be measured. This is not a limitation for the operation of the instrument.

The term "viscoelasticity" is understood to mean the mechanical properties of materials in term of both elastic and viscous behaviours when they are subjected to deformation or force. In Elasticity, storage shear modulus G' or Young's modulus E', represents the ability of a material to store the deformation energy. The behaviour of an elastic material is simply explained by its capacity to recover its original shape after the end of the deformation or force. On the other hand, the viscosity, represented by the loss modulus G'' or E'', is the capacity of the material to dissipate deformation energy as heat. In the temporal domain, viscoelasticity can be characterized by the creep and relaxation functions of a material. These functions can be calculated and displayed by the instrument after the spectral characterization of a material.

Spectroscopic measurement of viscoelasticity is understood to mean measuring material elasticity and/or viscosity as a function of the frequency of excitation.

The applicants in the present invention demonstrated that an apparatus, a system and a method based on shear wave induced resonance technology, can be devised to dynamically measure the viscoelasticity of material samples or structures over a wide range of viscoelasticities, frequencies and geometries, in order to respond to a wide range of material testing requirements. Structures can be an assembly of elementary material samples, a complex multi-components material, composite material or a multi-phase material. Such structures shall also be deemed designated hereinafter by the general terms samples or material samples. The present invention thus concerns a hyper-frequency spectroscopic viscoelasticity apparatus usable with a variety of material samples and confinement or holder configurations adapted thereto, according to a plurality of user selectable viscoelasticity measurement modalities.

The material sample can be confined into a sample container (holder) of known shape like a cylinder of arbitrary cross-section and length, a parallelepiped, a cube or a disk. The container vibrations propagate shear waves into the confined material in order to potentially induce mechanical resonances. The sample container may or may not have a bottom. The material sample may also be attached to a single holder or to multiple vibrating holding supports transmitting vibrations to induce shear waves into the measured sample. Holding means with different attachments may be provided to hold elongated linear material samples like beams and tubes of arbitrary cross-sections, material with different cross-section shapes that vary along the sample's length, or two-dimensional material samples like plates, membranes or shells. However, an essential imperative is to use rigid sample holding means that will transmit vibration from a vibration generator to the sample without generating undesirable waves in the holder. Therefore, rigid sample holding means such as metallic (ex. Aluminum) containers, frame or support may be used to present much higher rigidity than the tested material.

The apparatus according to the present invention may use a non-contact set-up to measure the material sample vibrations resulting into a given excitation. The non-contact set-up measures the temporal response of the material and calculates its spectral response.

Therefore, in accordance with an illustrative embodiment of the present invention as broadly claimed, there is provided a system for dynamically measuring viscoelasticity of material samples or structures using shear wave induced resonance, the system comprising: i) an apparatus comprising a vibration source; a vibration detector; a processor, and a user interface for selecting a sample holder configuration, and ii) sample holding means connectable to the vibration source, wherein the vibration source generates shear waves that induce vibrations and the resonance of a sample through the holding means, the vibration sensor measuring the sample vibrations and resonances, and the processor determining the viscoelasticity of the sample from said vibrations and resonances and from the selected sample holder configuration.

According to an aspect of the invention, the vibration sensor may comprise a non-contact sensor and the apparatus may further comprise an environmental chamber (to control temperature, humidity, pressure, etc. or to ensure the immersion of the sample in a liquid or a gas) adapted to confine a sample and at least part of the sample holding means, said chamber being provided with a window to enable functional contact between the sensor and the sample.

According to another aspect of the invention, the user interface may enable a user to select one or more predetermined test modalities whereby the processor may execute a test sequence as a function of the selected modalities. Predetermined modalities may be selected from the group comprising: time parameters; temperature parameters; strain parameters; repetition parameters and mapping parameters.

According to a further aspect of the invention, the sample holding means may comprise a container for confining the sample. The container may have a cylindrical shape of variable height and defining any mathematically determinable cross-section shape. The container may be exempt of a bottom if material sample has appropriate dimensional stability.

According to another aspect of the invention, the sample holding means may comprise a conformable frame assembled to a perimeter of the sample.

According to a further aspect of the invention, the sample holding means may comprise one or a plurality of supports firmly attachable to the sample. These supports can define a plurality of sample portions firmly held at material sample or structure so to allow measurements to be sequentially performed at any of said sample portions.

According to another aspect of the invention, the sample holding means may comprise a pair of upper and lower symmetrical plates defining a plurality of opening, whereby a material sample in flat and relatively thin (ex. plates or sheets) form may be inserted between the plates to define a plurality of sample portions firmly held at their perimeter so to allow measurements to be sequentially performed at any of said sample portions.

According to some embodiments of the invention, there is provided a system for dynamically measuring viscoelasticity of material samples or structures using shear wave induced resonance, the system comprising:
  i) an apparatus comprising a vibration source;
  a vibration detector; and
  a processor, and
  ii) a rigid sample holder connectable to the vibration source,
    wherein the vibration source induces vibrations or the resonance of a sample through the holder, the vibration sensor measures the sample vibrations and resonance, and the processor determines the viscoelasticity of the sample from the vibrations or resonances and from a sample holder configuration.

According to an embodiment of the invention, there is provided a method for dynamically measuring viscoelasticity of material samples using shear wave induced resonance, the method comprising: mounting at least one material sample to holding means (i.e. a rigid holder); selectively inducing resonance to the sample by applying selected vibrations to the holding means (i.e. the rigid holder); measuring the vibrations and resonances of the structure (i.e. the material sample in the rigid holder) to obtain at least one of: displacement, velocity and acceleration spectra; and deriving the viscoelastic properties of the sample from the measured spectra and from sample's geometrical shape and precise dimensions. The method may further comprise selecting at least one from a plurality of testing modalities.

Indeed, the geometrical shape and the dimensions of the material samples or structures to be tested by the apparatus have to be precisely known to properly correlate the viscoelastic properties of the sample with the measured spectra. The material sample or structure has to be confined into a sample container or firmly held by mechanical supports (the holding means) collectively designated as the sample holder in the following. The sample holder is mechanically very stiff comparing to the tested material sample or structure. The sample holder and the material sample form the excited system. The vibration source and the mechanical vibration source can be considered as a system generating shear waves into the material sample. The excited system is connected to a vibration source generating transient, harmonic or any constructed signal. The sample holder vibrates exactly as the vibration source and generates at its interface with the material sample or structure propagating waves. The propagation of the waves into the material sample or structure can induce or not resonances of the sample. The vibrational response of the material sample or structure is measured and treated to extract the viscoelastic information by the monitoring and processing unit of the instrument. The present disclosure describes a set of sample holders which can be used with the apparatus to form a measurement system. The sample holder can be a cylinder or mechanical supports that maintain material samples and structures of different shapes: cylinders, disks, plates, membranes, shells and beams.

A further major aspect of the invention concerns the viscoelastic measurement modalities using the apparatus and system. These modalities can be selectively interlinked and combined to study a material sample or structure confined or held following a configuration as described above. The new measurement modalities that can be selected by a user using the apparatus are:
  time variation to measure temporal evolution of viscoelasticity of material samples or sample structures. This is done by the apparatus by performing viscoelasticity measurements at different times over a given time range.
  temperature variation to measure thermal effects on the viscoelasticity of material samples or sample structures. This is done by the apparatus by performing viscoelasticity measurements at different temperatures over a given temperature range.
  strain variation to measure the effect of applied dynamic strain on the viscoelasticity of material samples or sample structures. This is done by the apparatus by performing viscoelasticity measurements for different strain rates over a given range of dynamical ranges. This modality permits to study the non-linearity of materials.
  repetitive measurements for statistical analysis of material samples or structures viscoelasticity. This is done by the apparatus by performing multiple viscoelasticity measurements following a given repetition number.
  viscoelasticity mapping modality of material samples or structures. This is done by relatively moving the dynamical vibration non-contact measurement sensor to scan at multiple locations the viscoelasticity distribution over different portions of the material sample or structure.

The above described method for measuring viscoelasticity can also be applied to a method of manufacturing a product having a component made from a viscoelastic material requiring predetermined viscoelastic properties. In this way, the method comprises dynamically measuring viscoelasticity of the component according to the any one of the above-described methods to determine the viscoelastic properties. The product is then released if the viscoelastic properties measured correspond to the predetermined viscoelastic properties, or alternatively, the product is simply graded according to quality control procedures.

It will be appreciated that the illustrative embodiments of the present invention described herein generally obviate the limitations and drawbacks of the prior art systems and methods. In some cases they enable testing of a wide variety of material types being available as samples with different geometries and adapting data processing accordingly to ensure reliable measurement in any condition. Moreover, it will be appreciated that some embodiments of the invention enable testing material samples in different environmental conditions and in a plurality of modalities to obtain complete and significant test results.

BRIEF DESCRIPTION OF THE DRAWINGS

The invention will be better understood by way of the following detailed description with reference to the appended drawings, in which:

FIG. 1A is a schematic, part break-away, perspective view of an instrument for hyper-frequency spectroscopic viscoelasticity using shear wave resonance induction;

FIG. 1B is a side elevation sectional view of the apparatus of FIG. 1A;

FIG. 1C is a front elevation sectional view of a variant embodiment of the instrument;

FIG. 2A is an illustration of a material sample confined in a cylindrical sample holder with a circular cross-section, in which shear waves are transmitted by the sample holder to the material;

FIG. 2B is an illustration of a material sample confined in a cylindrical sample holder with a rectangular cross-section, in which shear waves are transmitted by the sample holder to the material;

FIG. 3A is an illustration of a material sample confined in a cylindrical sample holder with an arbitrary cross-section, in which shear waves are transmitted by the sample holder to the material;

FIG. 3B is an illustration of a material sample confined in a vertical parallel plates sample holder, in which shear waves are transmitted by the sample holder to the material;

FIG. 4A(a) is an illustration of a material sample confined in a sample holder of circular plate shape;

FIG. 4A(b) is an illustration of a material sample confined in a sample holder of rectangular plate shape;

FIG. 4A(c) is an illustration of a material sample or structure confinement using a support of circular shape in which the material forms a circular plate or membrane;

FIG. 4A(d) is an illustration of a material sample or structure confinement using a support of rectangular shape in which the material forms a rectangular plate or membrane;

FIG. 4B is an illustration of a plate or membrane material sample or structure confinement between two hollowed or rectangular aperture-bearing plate supports for hyper-frequency spectroscopic viscoelasticity mapping;

FIG. 4C is an illustration of a plate or membrane material sample or structure confinement between two hollowed or circular aperture-bearing plate supports for hyper-frequency spectroscopic viscoelasticity mapping;

FIG. 5A(a) is an illustration of a material sample or structure confinement using supports to form a beam with rectangular cross-section, in which shear waves are transmitted by the vibrations of the sample supports to the material sample or structure;

FIG. 5A(b) is an illustration of a material sample or structure confinement using supports to form a beam with circular cross-section, in which shear waves are transmitted by the vibrations of the sample supports to the material sample or structure;

FIG. 5B(a) is an illustration of a material sample or structure confinement using simple supports on both sides to form a beam, in which shear waves are transmitted by the vibrations of the sample supports (or connections) to the material sample or structure;

FIG. 5B(b) is an illustration of a material sample or structure confinement using full moment connection supports to form a beam, in which shear waves are transmitted by the vibrations of the sample supports (or connections) to the material sample or structure;

FIG. 5B(c) is an illustration of a material sample or structure confinement using a simple support on one side and a full moment support on the other side to form a beam, in which shear waves are transmitted by the vibrations of the sample supports (or connections) to the material sample or structure;

FIG. 5B(d) is an illustration of a material sample or structure confinement using a full moment support on one side to form a cantilever beam, in which shear waves are transmitted by the vibrations of the sample supports (or connections) to the material sample or structure;

FIG. 12 is a plot of Young's modulus (MPa) as a function of position along a sample beam with the sample beam shown above the plot;

FIG. 13A is a 3D plot of elasticity G' in kPa as a function of frequency in Hz and time during polymerization of the material sample, in which the material's viscoelasticity evolution is targeted between 100 and 1200 Hz and 30 to 90 minutes in time;

FIG. 13B is a 3D plot of viscosity G" in kPa as a function of frequency in Hz and time during polymerization of the material sample, in which the material's viscoelasticity evolution is targeted between 100 and 1200 Hz and 30 to 90 minutes in time;

FIG. 14A is a temporal plot of displacement of a material obtained by the instrument;

FIG. 14B is a frequency plot of displacement of a material obtained by the instrument; and FIG. 14C (appearing on the sheet with FIG. 12) is a plot of amplitude ratios for different strain values ($\epsilon$) at different frequencies to indicate the non-linear dynamic behavior of the material sample or structure using the strain-parameterized modality.

DETAILED DESCRIPTION

Figure 6:
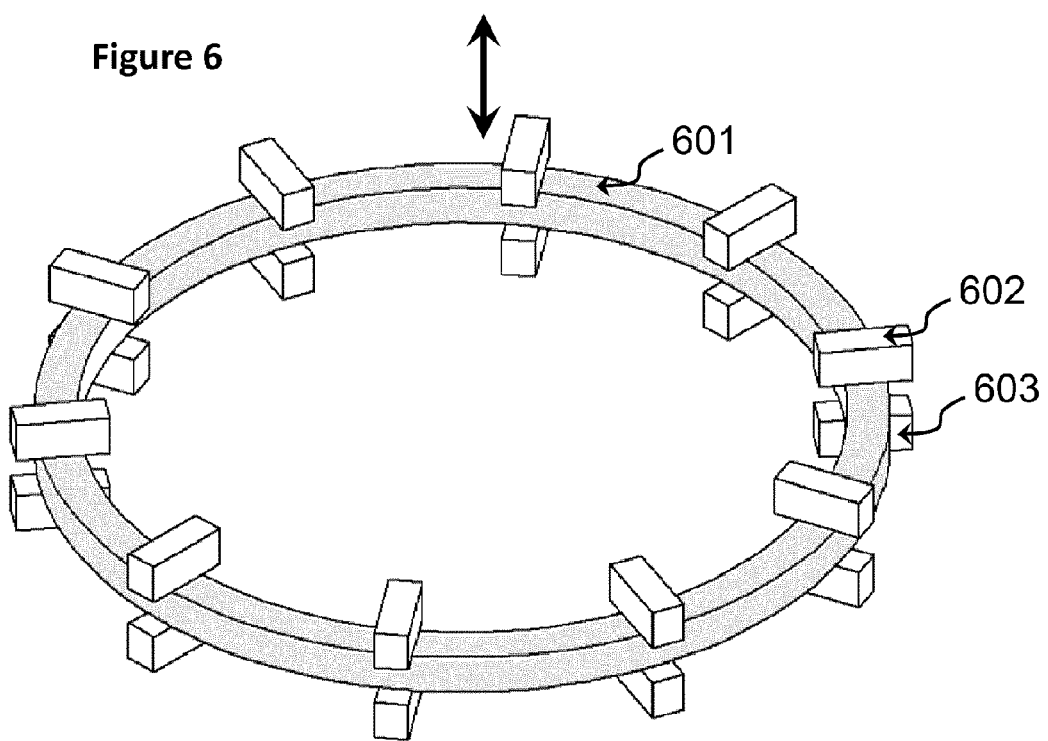
FIG. 6 is a perspective view of a material sample or structure (shown in a ring configuration) confined by multiple supports for hyperfrequency spectroscopic viscoelasticity mapping, in which shear waves are transmitted by the vibrations of the sample supports to the material sample or structure.

FIG. 1A gives an implementation example of a system and apparatus according to the invention. The apparatus is supported by a rigid and anti-vibration structure 10. The measurement of the dynamical vibrations of the material sample or sample structure is performed without contact by the vibration sensor 12 connected to an actuator 11 allowing a three-dimensional displacement of the sensor. The material sample or structure contained in a sample container, holder or attached to supports 14 can be confined in a thermal chamber 15 for thermal controlling containing a measurement window 13 for non-contact measurement of dynamical vibrations. Without being limited to one specific type of non-contact vibration sensor 12, a laser sensor from MicroEpsilon can be used. The sample container, holder or supports 14 are connected to a vibration source 16 which can translate in three-dimensions. The instrument is supported by anti-vibration supports 17. The apparatus' functions and operations are controlled and monitored by the processing unit 18 in order to control, regulate, measure, calibrate, amplify and condition the signals, calculate, process, store, interface and display.

FIG. 1B is a side schematic view of the instrument for hyper-frequency spectroscopic viscoelasticity using shear waves resonance induction.

FIG. 1C shows a two-dimensional front view of a variant of the instrument containing two supporting lateral beams 10 connected to a transverse beam 11 to which is connected a vibration sensor 12. The support 11, the sensor 12 and the vibration source 16 can be translated.

The container 14 is connected to a mechanical vibration source 16 (FIG. 1). These two joined elements constitute a single vibrating system (object). The material is contained into the container. The contact surface between the material and the container depends on the type of container. When the system container-vibration source is vibrating, dynamic mechanical excitation is transmitted to the material through the contact surface. This energy transmission gives rise to propagating mechanical waves into the material. These waves can be shear waves, flexural waves, compression waves, torsional waves or any combination of these waves. By the propagation of these mechanical waves, steady waves can appear in the tested material and its eigenmodes can be excited.

FIG. 2A illustrates a circular cylinder 202 containing a material sample 201 to be tested in viscoelastic spectroscopy using the apparatus. FIG. 2B gives an example of material sample 210 to be tested in viscoelastic spectroscopy using the apparatus and contained in a sample container 211 cylindrically shaped with a rectangular cross-section. In these two examples, shear waves are transmitted to the material samples 201 or 210 by the vertical vibration of the sample containers (or holders) 202 or 211. The dynamic response of the material sample is due to the transmitted shear waves and allows for its viscoelastic characterization.

It will be appreciated that the choice of sample geometry can be made to simplify the analysis of the vibration response for the purposes of viscoelastic characterization, or can be to simply sample preparation. Some materials can be molded into a desired holder shape, while other materials are measured without modification, and others still are cut into beams or strips so that the holder can attach to them.

More generally, as described in FIG. 3A material samples 301 can be confined in cylindrical material containers of arbitrary and known cross-sections 302 to be tested in viscoelastic spectroscopy using the apparatus. Shear waves are transmitted to the sample 301 by the vibration of the sample holder 302. Dynamical response of the material sample serves to its viscoelatsic characterization.

Another geometry tested by the instrument is given in FIG. 3-B in which the sample 303 has the geometrical shape of a slice or a sheet of a known thickness. The sample is fixed between two plates constituting the sample holder 304. The plates can have a selected spacing to define an initial amount of compression of the material, and are mounted solidly together to receive the vibration. The sample holder is connected to vibration source and its vibration generates at the interface with the sample, propagating shear waves. Dynamical response of the material sample serves to its viscoelatsic characterization. The container plates are in contact with the two largest material sample surfaces and the mechanical vibrations are transmitted to the material by the interface between the material and the holder rigid plates. The holder rigid plates are vibrating in phase. The holder-vibration source system vibrates and generates shear waves into the slice. The vibration of the material sample is measured in the free surface which is perpendicular to the container plates and to the vibration direction. The sample can be cut from the raw material or poured in a dedicated mould to form the appropriate geometry.

The distance between the plates confining the material sample can be adjusted to apply a static stress or strain. These static stress or strain can be selected by the user to be zero. The application of such static strain or stress can serve to study and characterize the non-linear behaviour of materials.

Other configurations are given in FIG. 4A. In FIG. 4A(a) the material sample 401 to be tested using the apparatus is a circular plate contained in a solid sample low profile cylindrical holder of circular shape 402. In FIG. 4A(b) another example is given of a material sample 403 having the shape of a rectangular plate confined in a low profile rectangular shaped sample container 404. In both examples of FIG. 4A(a) and FIG. 4A(b), the vibration of the material sample container generates propagating shear waves into the material sample. The propagation of shear waves can induce resonances of the material sample. The resulting material sample vibration, even for non-resonant vibrations, serves to measure its spectroscopic viscoelasticity using the apparatus. Examples given in FIG. 4A(a) and FIG. 4A(b) are not restrictive. Indeed, the shape of the material sample and the container, under the same mechanical configuration described in FIG. 4A(a) and FIG. 4A(b), can be arbitrary.

FIG. 4A(c) gives another configuration to test material samples or structures mounted to holders by the apparatus to perform spectroscopic viscoelasticity measurements. The object under testing can be a material sample or a structure 405 forming a plate or a membrane connected to a supporting frame of circular shape 406 vibrating vertically and transmitting shear waves to the periphery of the material sample or structure under testing. FIG. 4A(d) is another example of a material sample or a structure having the geometry of a rectangular plate or membrane 407 supported by a peripheral rectangular supporting frame 408 transmitting vertical vibrations to the tested body 407. The two geometrical and mechanical configurations of FIG. 4A(c) and FIG. 4A(d) can be generalized to plates or membranes of arbitrary shape.

As shown in FIG. 4B, a holder system is composed of two identical rigid plates (410 and 412) each defining an array of square or rectangular holes or apertures. The material sample or structure 411 is sandwiched between the two rigid plates. The plates 410 and 412 are aligned in registration with each other. As a result, during the vibration applied similarly to 410 and 412 in the direction defined as perpendicular to the sample larger surface, the sample portions positioned in the square or rectangular holes vibrates and moves in the direction of the vibration direction due to shear waves propagation. Using the apparatus, the induced vibration spectrum pattern is used to determinate the sample viscoelasticity at the different portions. The configuration of FIG. 4B can serve to perform the viscoelastic mapping of the material sample or structure.

As shown in FIG. 4C, the system is composed of two identical rigid plates with circular or elliptical holes (413 and 415). Between the two rigid plates are sandwiched the material sample or structure 414. The plates 413 and 415 are aligned and registered with each other. As a result, during the vibration applied similarly to 413 and 415 in the direction defined as perpendicular to the sample larger surface, the sample portions positioned in the circular or elliptical holes vibrates and moves in the direction of the vibration direction due to shear wave propagation. Using the apparatus, the induced vibration spectrum pattern is used to determine the sample viscoelasticity at the different portions or locations. The configuration of FIG. 4C can serve to perform the viscoelastic mapping of the material sample or structure. In the case of destructive testing, the sheet 411 or 414 can be a slice cut from a larger piece of material, and the properties of the material at the location of each aperture are measured from the sheet.

FIGS. 5A(a) and 5A(b) give examples of material samples or structures to be tested using the instrument to perform viscoelastic spectroscopy. In FIG. 5A(a) is given the example of a material sample or structure having the shape of a beam with rectangular cross-section 501 attached to two vibrating supports 502. FIG. 5A(b) illustrates the case of a material sample or a structure 510 to be tested by the apparatus and having the geometry of a beam of circular cross-section connected to vibrating supports 511 to propagate shear waves and vibrations into the material. More generally, the tested beams can have arbitrary cross-sections and can be hollow. Some of the possible supports or connections configurations are shown in FIGS. 5B(a) through 5B(d). The beam under measurement by the apparatus can be simply supported on both sides 520, supported by full moment connections on both sides 521, simply supported in one side and attached to a full moment connection in the other side 522 or attached to a full moment connection in one side to form a cantilever beam 523. Shear waves are transmitted by the vibration of the supports (or connections) to the material or structure to perform viscoelastic spectroscopy using the apparatus.

The system presented in FIG. 6 comprises a rectangular cross-section, annular sample 601 to be characterized (the geometry and dimensions can be as defined in 501 or 510), and the sample holders or containers 602 and 603 employed to transmit shear waves to the sample. The components 602 and 603 are also presented at different arbitrary locations around the sample and can be any support of those presented in FIGS. 5B(a) to 5B(c). The section of the sample 601 can be defined as rectangular, squared, elliptical, hollow cylindrical, or cylindrical, for example, or with any geometries known in the art. The sample 601 can be a cylindrical, rectangular, or elliptical ring, for example, or of any geometries known in the art. The measurement of the viscoelasticity of the sample 601 with the system in the FIG. 6 is done using the apparatus and can serve to perform viscoelasticity mapping.

The above embodiments offer to deal with a wide variety of containers, or sample holders. The phraseology and terminology used in the following is for the purpose of description and should not be regarded as limiting:

Cylindrical (FIG. 2, FIG. 3-A) or circular/rectangular plate shape (FIG. 4-A) container can contain sample exhibiting, for example, very soft to very hard viscoelasticity. This holder is well adapted for samples that can be poured in the container or casted in moulds and then inserted into the container. The cylindrical shape sample, inserted in the container can also be obtained from raw material using a dedicated extractor. A sample, originally of cylindrical shape, can also be inserted in the holder.

Hollowed plate support (FIG. 4-B, FIG. 4-C) is dedicated for thin or thick soft or hard samples having homogeneous thickness. The sample can be cut from the raw material or poured in a dedicated mould.

Beam (FIG. 5-A, FIG. 5-B) with rectangular or circular cross-section is optimized for hard and very hard sample. The sample can be cut from the raw material or poured in a dedicated mould.

Slice (FIG. 3-B) with rectangular cross-section is well adapted for very soft and soft samples. The sample can be cut from raw material.

Annular sample material or structure (FIG. 6) can be directly connected to the multiple supports holder. The sample can be cut from raw material or casted in a mould.

After the selection and the preparation of the sample to test, the user inserts or pours the sample into the selected container and designated as sample holder. The sample can be rectangular like a slice (FIG. 3-B), a beam (FIG. 5), a plate, a film (FIG. 4), cylindrical FIG. 2 A-B, FIG. 3-A or of any shape. The container is then firmly connected to the vibration source FIG. 1.

The user can, using an interface, select the geometry, the measurement modalities and parameterize the test (i.e. repetition time, temperature, strain, etc.). In another configuration of the instrument it is not necessary to select a geometry or modality and start the measurement. Indeed, the instrument can integrate a unique geometry which does not need a user interaction to start the measurements. The latter are made automatically and can be performed for quality control of products or research and development purposes. This is the stand-alone version of the instrument.

The measurement sensor (in FIG. 1) is manually, semi-automatically or automatically positioned in proximity of the sample to measure the displacement of the tested sample during and after the mechanical vibration induced in the sample using the container-vibration source system. The results, evolution of the viscoelasticity as function of frequency and/or time (time parameters) and/or temperature (temperature parameters) and/or strain (strain parameter) and/or repetition time (repetition parameter) and/or space (mapping parameters) is displayed on the software interface or stored and displayed in a more global information system.

The spectral viscoelastic properties of the material are obtained from the displacement of the sample and its known geometry. The temporal displacement is measured in a single or multiple known positions and can be recorded or not. Any sampling strategy or signal processing method can be used to enhance the signals quality. These displacement signals are processed to be transformed in the frequency domain using any known transformation method. The measured displacement spectrum (or spectra) over a given frequency range serves to obtain the viscoelasticity of the sample. The experimental spectrum is compared to a calculated spectrum using a numerical procedure (like the difference minimization or any such method known in the art) to obtain the viscoelastic properties (spectrum or single spectral value) of the sample over the whole frequency range of interest. The calculated spectrum is obtained from a dedicated numerical or analytical model simulating the vibration of the sample knowing: its geometry, its boundary conditions, the excitation and the spatial position of the measurement. The viscoelastic spectra are then plotted or processed to get the creep or relaxation curves that characterize the viscoelasticity of the sample in the time domain.

It is important to note that the inertia of the material sample plays an important role in the vibration and resonance generation in the sample. The different holders described here transmit a mechanical excitation to the material sample through the boundaries. Then, the inertia of the sample will cause its free vibration and the appearance of resonances. This free vibration, due to inertia effects, is used to characterize the viscoelasticity of the material.

In the case of the circular cylindrical geometry of the instrument (FIG. 2-A), having a radius R, the displacement of the material sample U in the center of the cylinder is given by the following equation:

$$U(f) = \frac{A(f)}{J_0(kR)} \text{ with } k = \frac{2\pi f}{\sqrt{\frac{G(f)}{\rho}}}$$

Where A(f) is the spectral excitation (or stimulation) which is function of frequency, f is the frequency, $\rho$ is the density, G(f) the shear viscoelatic modulus of the material which is function of frequency: G(f)=G'(f)+iG"(f), and I is complex number with $i^2=-1$. $J_0$ is the Bessel function of the first kind of order 0. The calculated spectrum (or model) depends on the geometry (beam, slice, plate, membrane, etc.) used in the instrument and can be obtained by analytical or numerical approaches.

While the above mathematical expressions relate to the frequency domain, it will be appreciated by those skilled in the art what mathematical expressions to use when working in the time domain, in which the physical quantity of amplitude, velocity or acceleration is measured and recorded over time. It is also appreciated that similar or equivalent information can be obtained from frequency domain and time domain measurements and calculations, although in some circumstances, one approach can have advantages over the other, either in terms of the mathematical calculations or in terms of the facility of instrumentation and measurement.

If multiple displacement measurements are performed in multiple positions in the sample, the spatial information (or its transformation in the spectral domain) can also serve to obtain the viscoelastic properties of the tested material. Compared to the temporal case, a similar procedure can serve to compare and minimize the differences between experimental and simulated data. The viscoelastic spectra are then plotted or processed to get the creep or relaxation curves that characterize the viscoelasticity of the sample in the time domain.

Displacements can be measured by contact (like accelerometers, ultrasound) or non-contact technologies (ultrasound, laser interferometers, microphones, capacitance measurement systems, . . . ). The vibration source can be a pneumatic, piezoelectric, a shock generator or an electromagnetic shaker. An example is to use a laser sensor from MicroEpsilon to measure the displacements and vibrations produced in a silicone cylindrical sample material contained in a hollowed cylinder. The sample container (cylinder) can be connected to a shaker from LDS to generate vibrations. In this example, communication with functional parts of the instrument (sensor and vibration source) can be performed by a generation/acquisition electronic card connected to a computer. A software (computer program integrating the appropriate treatments, calculation and minimization solving algorithms) can be implemented in the computer to perform the adapted processing (described above) to the signals and obtain the viscoelastic properties of the material. The software can be programmed using languages like C++, Fortran or any dedicated computer language.

The processing unit and communication unit can be a computer, a microprocessor, a microcontroller, a Digital Signal Processor (DSP), a Field-Programmable Gate Array (FPGA) or any electronic or electric board.

The user can then manipulate the graphics and/or post-process the data and/or archive the data. Finally, the user has to disconnect the sample holder from the vibration source and remove the sample from the container for further measurements.

In the aerospace industry, the user is interested to know the evolution of elasticity and viscosity of attenuating material to see, for example, if the said material dissipates energy in the frequency band generating important noise or reduces the artefactual vibration that could destabilise the plane. Another utility of such measurement in the automobile industry is to test the ability of designed tire to be enough stiff at high temperature to explore its behaviour in real conditions. Another non-limiting example is in quality control of implantable biomaterials to detect defects when local viscoelasticity is different than the rest of the sample. Such local viscoelastic heterogeneity can be a failure zone potentially dangerous for the patient.

Figure 7:
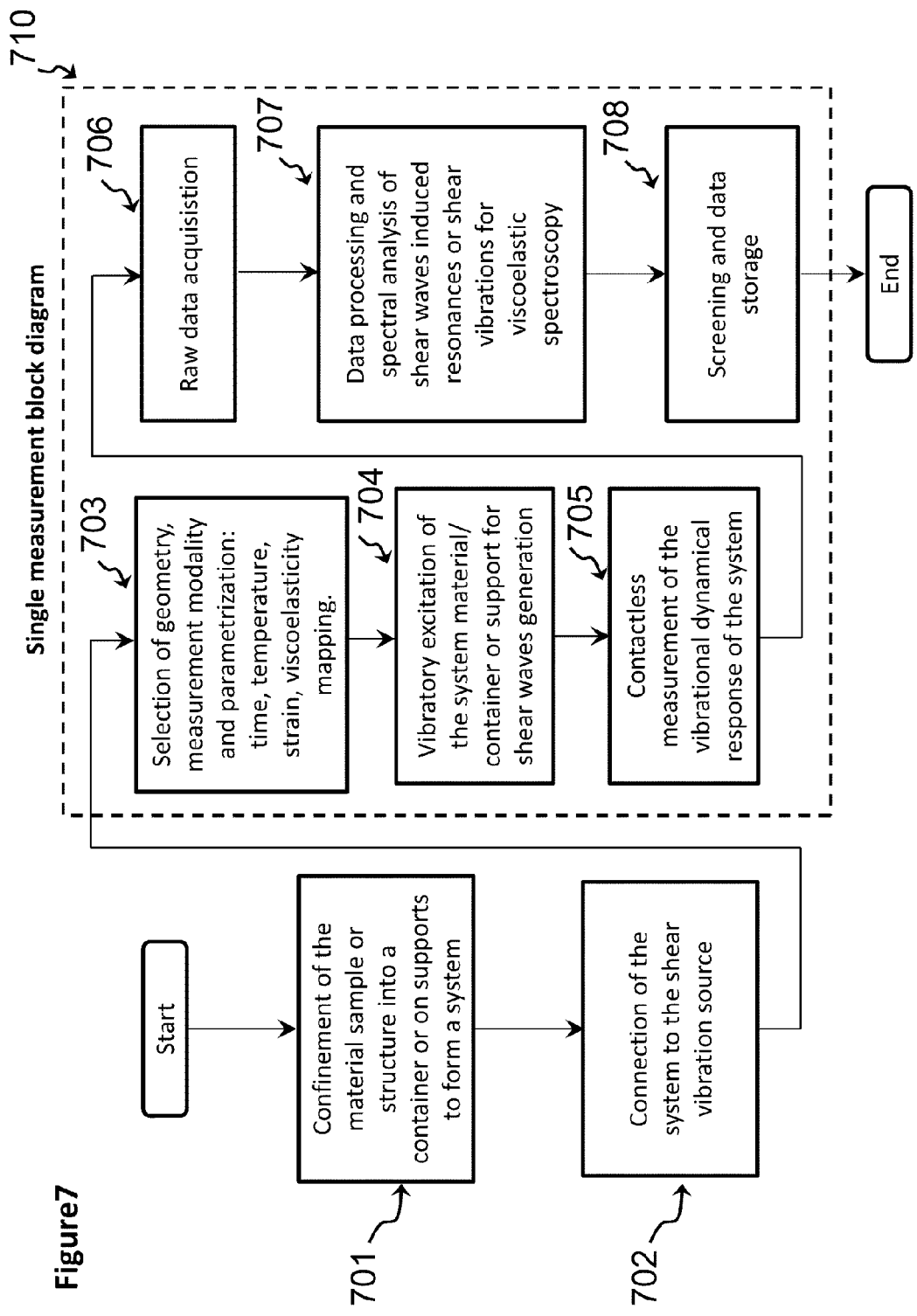
FIG. 7 is a flowchart of a typical viscoelastic spectroscopy measurement on a single material sample using the instrument.

FIG. 7 is a flowchart of a typical viscoelastic spectroscopy measurement on a single material sample using the instrument. First the material sample or structure is confined into a container or attached to supports to form the excited system 701. This system is then connected to a mechanical vibration source for shear wave generation 702. The apparatus offers to select and to parameterize the viscoelastic measurement modality in geometry, time, temperature, strain or viscoelastic mapping 703, or with a combination of one or more of these modalities. Then, a vibration excitation is applied to the sample-holder in order to generate shear waves in the material 704. The measurement of the vibrational dynamic response of the system is then remotely realized without contact 705, and the raw data are acquired 706. Data processing and spectral analysis of shear waves induced resonances or shear vibrations, 707, serves to perform viscoelastic spectroscopy of the material sample or structure under testing. Finally, before ending the process and depending on the selected measurement modality, the viscoelastic results are displayed and stored 708. The steps 703, 704, 705, 706, 707 and 708 constitute the fundamental steps of the single measurement block diagram 710 which enters in the process of the apparatus' modalities.

Figure 8:
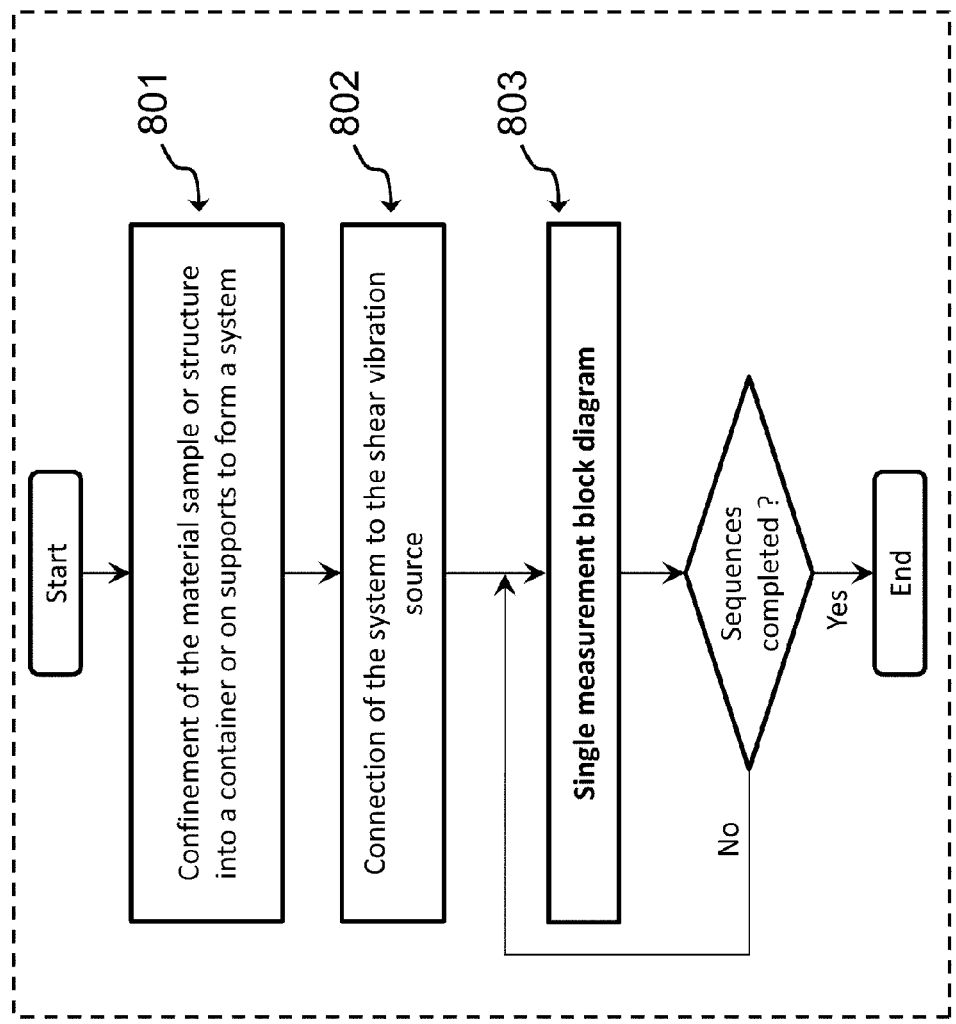
FIG. 8 is a flowchart of a sequence of viscoelastic spectroscopy measurements using the instrument according to some embodiments.

FIG. 8 is a flowchart of a sequence of viscoelastic spectroscopy measurements using the instrument and is defined as a measurement sequences block diagram 810. In step 801, information related to the system including the material sample or structure (i.e. as 201, 210, 301, 401, 403, 405, 407, 411, 414, 501, 510, or 601) which is confined in a holder, in a container (i.e. as 202, 211, 302, 402, 404, 406, 408, 410, 412, 413, or 415) or on supports (i.e. as 502, 511, 520, 521, 522, 523, 602, or 603). In step 802 is described the system which consists in connecting the system 801 to the shear vibration source. This connection is made with any action or component allowing to attach one or more systems (i.e. screw in, clip), or with any system known in the art. The step 803, described in more detail in 710, realized the modality selection and initialization, the data measurement, the post-processing and the display and storage of viscoelastic measurements. Step 803 is repeated until the selected measurement sequence is completed.

The system container-vibration source can vibrate or generate the different types of excitations. These excitations can be a harmonic excitation, a transient excitation or any combination of these two excitation types. The transient excitation can be a pulse which is a brief excitation having a large frequency spectral content (i.e a large bandwidth) with regard to the natural spectral response of the material. The excitation of a large frequency range is unique to the instrument since it serves to characterize by a single excitation and very quickly the viscoelasticity in a large frequency range. The transient excitation can also be a combination of several pulses with different frequency contents and shapes (sinus, cosines, triangle, square, . . . ).

Contrary to old generation instruments, the use of transient and pulse waves to excite and then to characterize the material viscoelasticity allows the instrument to perform very quick and precise measurements over a large frequency range. The rapidity of measurements is of great interest for many applications. For example, using the instrument and with a measurement time step of less than one (1) second, it is possible to monitor the rapid curing process of polymers, resins or glues. The measurement time step can be adapted to the material and process to be characterized.

The time monitoring of materials viscoelasticity evolution is greatly useful in research and development (R&D) to optimize the composition of new or existing materials to target an optimal curing time, polymerization profile and final stiffness. In addition, the rapidity of measurements combined to the contactless measurements allows using the instrument for bench or on-line (i.e. on production lines) Quality Control (QC) of industrial products. For example, the QC performed by the instrument allows to stop a curing process when the desired quality is reached and to optimize the curing time of industrial products to minimise manufacturing delays and increase the productivity.

The use of pulse excitations is also interesting to characterize and to study thermally induced viscoelasticity evolutions. This functionality is interesting for industries using thermal energy transfer to develop and produce products and materials. The rapid measurement of viscoelasticity by the instrument is a unique advantage to characterize and to monitor rapid thermally induced changes (curing temperature, curing time-profiles, glass transition, . . . ).

The instrument can serve to perform Quality Control in laboratory (off-line) and on the production lines (on-line). An example of QC in laboratory is to sample (randomly or sequentially) products or materials from the production lines or a production batch to test them in a laboratory using the instrument. A number of products or materials are sequentially set up in the instrument and tested to characterize their viscoelasticities following the instrument user instructions. Then, the viscoelasticities of products or materials can be statistically processed to evaluate the ratio or percentage of failed products or materials. If the failure ratio is higher than a fixed value (quality criteria fixed by the user), then the production batch is rejected, otherwise the production batch meets the industrial quality criteria and is qualified to be processed or commercialized.

On-line production QC using the instrument is also possible. The instrument is installed on or near the production lines and connected to a handling system (a robot, a mechanical arm, a mechanical sampling system or a mechanism) to extract products or material from the production line and to route them to the instrument. The handling system can extract 100% or a certain amount of products or materials. Then, the products or materials are tested using the instrument to characterize their current viscoelastic value. The viscoelastic value of each product or material is send to a processing system (computer software or a QC integrated system) that compare the current viscoelastic value to a reference value or range. If the current viscoelastic value does not meet the reference value or range, then the product or material is rejected. Otherwise, the product or material is qualified to be processed or commercialized. Another alternative for on-line QC of products or materials using the instrument can consist in testing on-line (following the previously described implementation) the viscoelasticity of several products or materials, to process them statistically and to decide whether a production batch meets or not a given quality criteria. The real-time information given by the instrument can also serve to automatically control the production process in a control loop by, for example, adjusting the quantity of input products, regulating the process temperature or humidity, etc.

Figure 9:
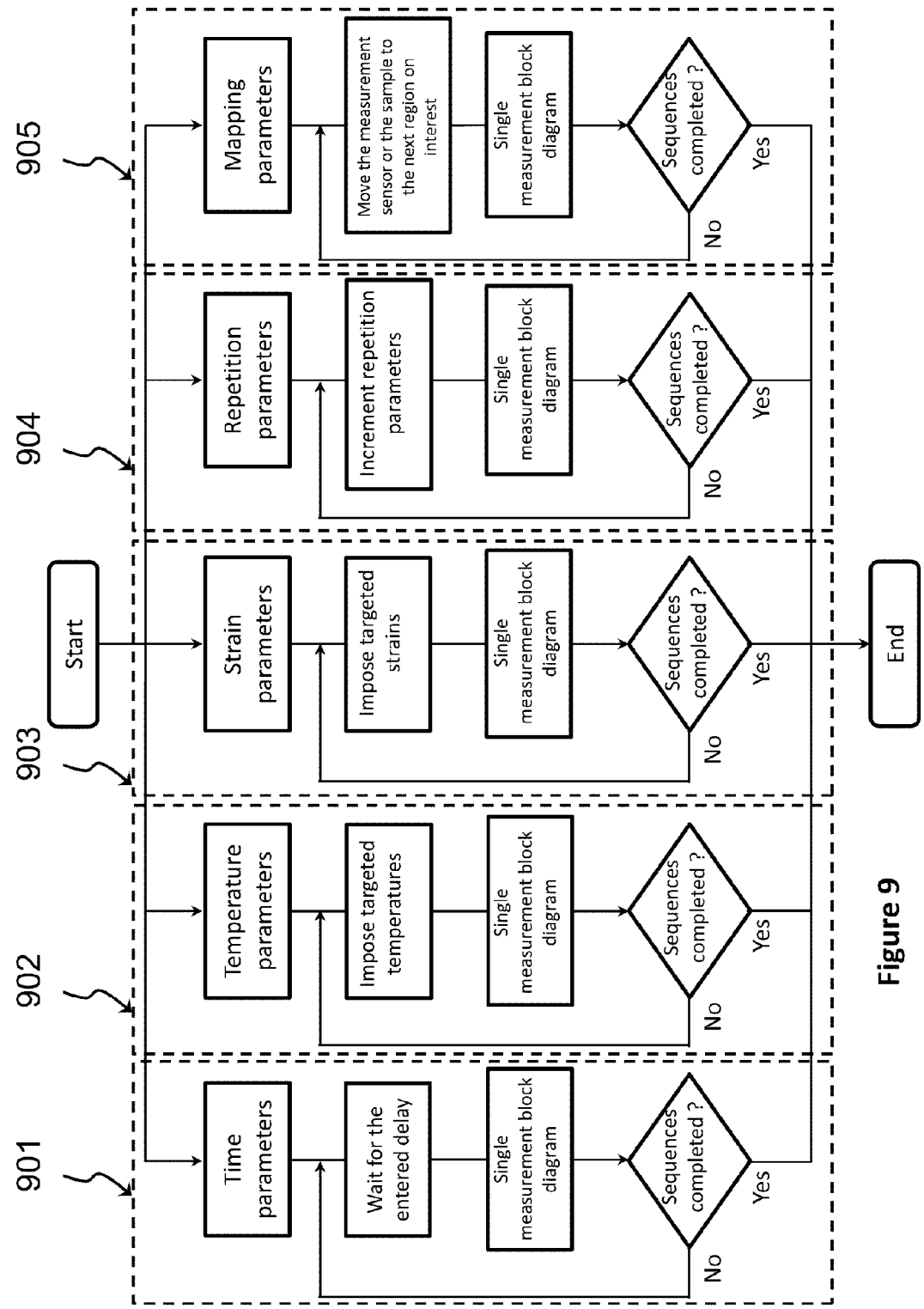
FIG. 9 is a flowchart of measurement modalities available using the instrument for the viscoelastic spectroscopy measurements according to some embodiments.

FIG. 9 is a more detailed flowchart of the modality selected and realized by the system 710. The viscoelastic spectroscopy measurement using the apparatus can be configured for different measurements as function of defined modalities parameters. The first modality 901 includes the setting of the time parameters, which are the time step coupled to the maximum duration of the experiment or the number of measurements in a period of time. The second modality 902 is the measurement of the sample viscoelastic characterization as function of temperature imposed around the sample and/or within the sample. The third modality 903 is based on imposed strain to the sample. This strain modality can be realized by a sequential tuning of the vibration amplitude imposed to the sample in order to reach a sample strain equivalent to the one entered as strain parameter. The fourth modality 904 is the repetitive measurement (arbitrary number of measurements) of the sample viscoelasticity simultaneously or quasi-simultaneously. These repetitive measurements permit a standard and/or statistical analysis. The fifth modality 905 allows obtaining the 1D and/or 2D viscoelasticity mapping of the sample by sequentially relatively moving the component used to realize the non-contact measurement, or by the displacement of the sample. All the above mentioned modalities can be interlinked each other. After the selection and the initialization of any of these modalities, the single measurement block diagram (as described in 710) is realized and the next step consists to iteratively repeat the measurement block until the condition entering in the modality parameters are satisfied.

The modality 901 outputs the viscoelastic spectroscopy measurement as function of time for the tested sample or structure. The modality 902 outputs the viscoelastic spectroscopy measurement as function of temperature for the tested sample or structure. The modality 903 outputs the viscoelastic spectroscopy measurement as function of strain for the tested sample or structure. The modality 904 outputs the viscoelastic spectroscopy measurement for one or more measurements for the tested sample or structure. The modality 905 outputs the map of the viscoelastic spectroscopy measurement of the tested sample or structure.

Figure 10:
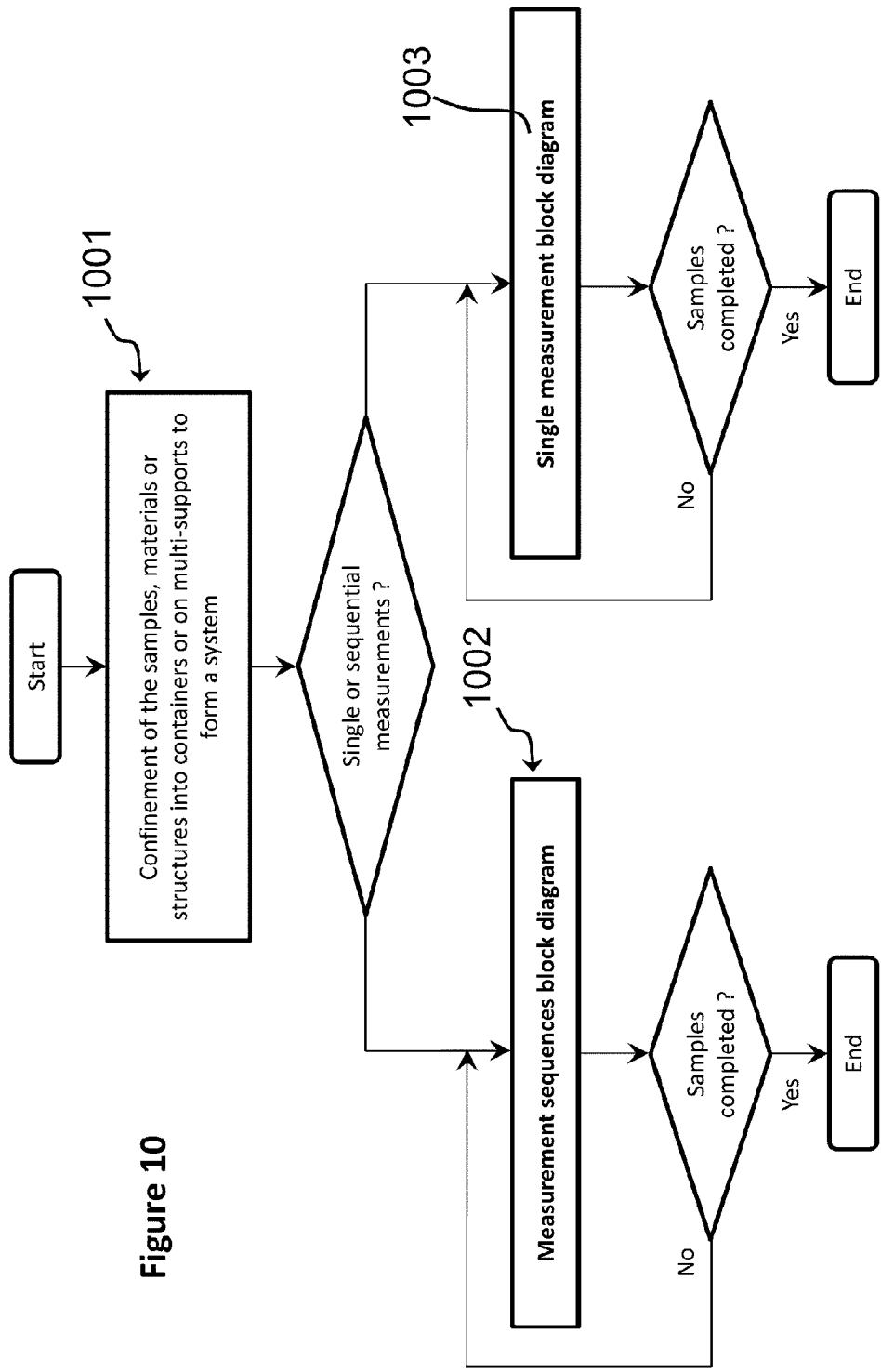
FIG. 10 is a flowchart of viscoelastic spectroscopy measurements combining the multiple samples modality and sequences using the instrument according to some embodiments.

FIG. 10 shows a flowchart of viscoelastic spectroscopy measurements combining the multiple sample modality and sequences using the instrument. The confinement of the material samples or structures into holders, containers or on multi-supports form the excited system 1001. In the case of the sequential measurement selection, the measurement sequences block diagram 1002, described in more detail in 810, is the sequence used for the viscoelastic spectroscopy measurements using the apparatus. Whereas the case of single measurement follows the protocol of the single measurement block diagram 1003, also described in 710. For any of the two cases, 1002 or 1003 are repeated until measurements of the samples are completed.

The hyper-frequency viscoelastic spectroscopy can be done as a function of:

Time (FIGS. 8 and 9): for materials having mechanical parameters evolving in time. For example, solidification of glues, epoxy, polymer, or any materials presenting such behavior. Viscoelastic parameters are important to optimize the chemical composition of material to better satisfy the conditions of utilisation regarding the profile of solidification, hardening rate or final viscoelasticity.

Temperature (FIGS. 8 and 9): to measure material viscoelasticity when the temperature imposed to the sample is fixed or evolving over time. This is important to know the apparent elasticity of material for different temperature and, for example, the glass transition temperature when the material exhibits a sudden dramatically increase of viscosity G" and decrease of elasticity G'. The user can also choose this modality to artificially accelerate aging in materials to see how the material viscoelasticity will behave in weeks, months, years even decades later.

Strain (FIGS. 8 and 9): to measure the effect of strain level on material viscoelasticity. In a nonlinear regime, materials often present different viscoelasticity as function of level of deformation. This information is important to develop or optimize safe products, for example when the materials are subjected to high amplitude deformation such as present in many applications (i.e. mechanical behavior of airplane tires during landing or car tires during a bend).

Repetition time (FIGS. 8 and 9): to increase the measurement accuracy and to evaluate the test reproducibility for further statistical analysis. The user can select this modality to acquire many times, sequentially or simultaneously, the viscoelastic spectroscopy of the sample. This modality results in a clear increase of productivity. This modality allows also to study the effect of mechanical fatigue on viscoelastic properties of materials. The repetitive excitation (i.e. number of cycles) can be monitored in strain by the instrument and this modality can be combined with the hyper-frequency viscoelastic measurements to characterize the material viscoelasticity as function of the mechanical fatigue.

Space mapping (FIGS. 8 and 9): to map, with a high spatial resolution, the viscoelasticity of a product or material. The user is interested in this modality to localise and characterize non-destructively the defects of a sample or a product by analysing the distribution of viscoelasticity in space or to design and produce non homogeneous viscoelastic materials or products.

Environmental conditions: using chamber 15 shown in FIGS. 1A, 1B and 1C, humidity, ambient pressure (including vacuum conditions), pH, and immersion fluid type are examples of environmental conditions that can be changed while measuring their impact on viscoelastic properties.

Figure 11:
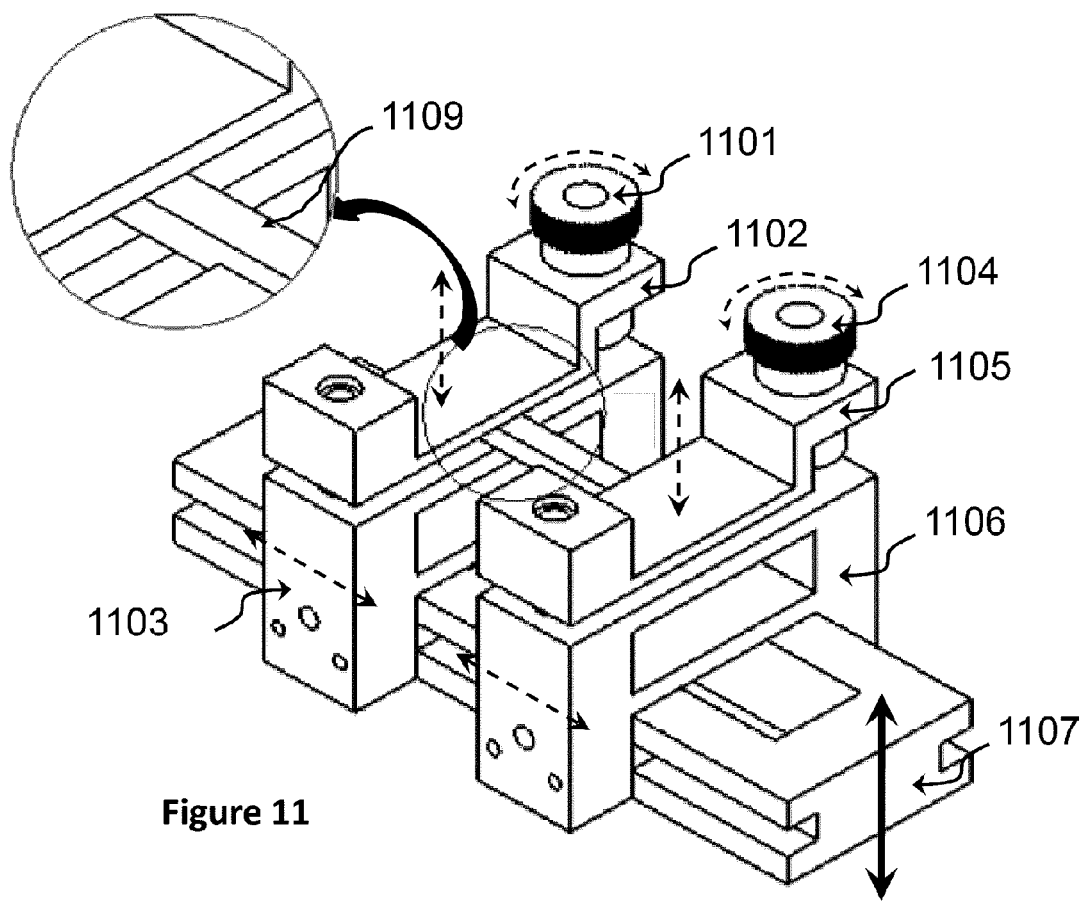
FIG. 11 is a detailed perspective view of the embodiment of system used to test material samples or structures supported with full moment connections on both sides, and using the instrument.

In FIG. 11, an example of the embodiment to FIG. 5A is illustrated with a 3D perspective detail view of the system used to test material samples or structures supported with full moment connections on both sides, and using the apparatus. The knobs 1101 or 1104, supported by the elements 1103 and 1106, can be rotated manually or automatically in order to induce the up or down displacement of the elements 1105 or 1102. The material sample or structure 1109 is sandwiched between the elements 1102 and 1103 in one side, and between the elements 1105 and 1106 in the other side. The elements 1103 and 1106 can be moved laterally along 1107 manually or automatically. The element 1107, on which is generated the source of vibration, supports the elements 1103 and 1106, which transmit the shear waves to the material sample or structure 1109.

FIG. 12 is an example of viscoelasticity mapping of a material sample or a structure using the viscoelasticity mapping modality 905 of the apparatus and viscoelastic spectroscopy measurement. FIG. 12 shows an example of the viscoelastic profile 1201 along a material sample or a structure 1202. The representation of the viscoelasticity of a structure (beam, plate, or sheet) can be done by a one-dimensional profile, a two-dimensional map (image) or in a three-dimensional volume (image).

FIG. 13-A shows an example of a three-dimensional representation of the spectral viscoelasticity evolution of a material sample during its polymerization using the time-parameterized modality 901 of the instrument. In this example, the material's storage shear modulus 1301 evolution is targeted between 100 and 1200 Hz in frequency and 30 and 90 minutes in time.

FIG. 13-B shows an example of a three-dimensional representation of the spectral viscoelasticity evolution of a material sample during its polymerization using the time-parameterized modality 901 of the instrument. In this example, the material's loss shear modulus 1302 evolution is targeted between 100 and 1200 Hz in frequency and 30 and 90 minutes in time.

FIGS. 14A, B and C are examples of dynamic viscoelastic non-linearity of a material obtained by the apparatus using the strain-parameterized modality 903. In FIG. 14-A, the sample material or structure temporal vibration 1401 due to shear waves propagation is given. In FIG. 14-B, this temporal signal is analyzed using spectral processing and displayed in 1402. In FIG. 14-C the above mentioned method is repeated for different strain values and the information contained in spectrum such as 1402 is used to recover the amplitude ratio 1403 of the frequencies f1, f2, f3 and f4 presented in 1402 and indicating the non-linear dynamic behavior of the material sample or structure.

One can thus appreciate from the foregoing description, that the system, apparatus and method of the present invention provide fast, accurate, simple, safe and cost efficient non-contact measurement of the viscoelastic properties of a wide range of material available as samples or structures of different shapes, in a plurality of test conditions.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

What is claimed is:

1. A system for dynamically measuring viscoelasticity of a material sample or structure using shear wave induced resonance having a sample stiffness, the system comprising:

an apparatus comprising: a vibration source, a vibration detector, and a processor operatively connected to and in data communication with the vibration detector; and a rigid sample holder having a sample holder configuration with an open bottom configured to support the material sample or structure, a holder stiffness stiffer than the sample stiffness and being engageable with the vibration source, the vibration source being actuable to induce vibrations to the rigid sample holder without generating undesirable waves therein, the vibration sensor measuring the vibrations or resonance induced to the material sample or structure through the rigid sample holder, and the processor determining the viscoelasticity of the material sample or structure from said measured vibrations or resonances and from the sample holder configuration.

2. The system as claimed in claim 1, further comprising a user interface for selecting the sample holder configuration and one or more predetermined test modalities whereby the processor can execute a test sequence as a function of the selected modalities.

3. The system as claimed in claim 2, wherein said predetermined modalities are selected from the group consisting of: time parameters; temperature parameters; strain parameters; repetition parameters and mapping parameters.

4. The system as claimed in claim 1, wherein the apparatus further comprises a housing defining a environmental chamber, the vibration source being at least partially contained inside the environmental chamber and the rigid sample holder being contained inside the environmental chamber and the vibration detector being located outside the environmental chamber.

5. The system as claimed in claim 4, wherein the housing defines a measurement window, and the vibration detector is oriented towards the measurement window.

6. The system as claimed in claim 1, wherein the vibration detector is a non-contact vibration detector and the vibration source is translatable in three-dimensions.

7. The system as claimed in claim 1, wherein the holder stiffness of the rigid sample holder is sufficient to vibrate as the vibration source.

8. The system as claimed in claim 1, wherein the rigid sample holder is exempt of a bottom.

9. The system as claimed in claim 1, wherein the rigid sample holder contacts the material sample or structure at at least one contact surface and the material sample or structure conforms to a shape of the rigid sample holder at the at least one contact surface.

10. The system as claimed in claim 1, wherein said rigid sample holder is a circular or non-circular cylindrical container having an open top.

11. The system as claimed in claim 10, wherein said material sample or structure is one of a plate, a sheet and a membrane, said material sample holder comprises a number of apertures providing a corresponding number of circular or non-circular cylindrical containers.

12. The system as claimed in claim 1, wherein said material sample or structure is a beam or cylinder, and said material sample holder supports said beam or cylinder at one of: a point spaced apart from a free end of said beam or cylinder; and two points on said beam or cylinder.

13. The system as claimed in claim 12, wherein said material sample holder is a cantilever material sample holder.

14. The system as claimed in claim 1, wherein said material sample or structure is annular in shape, and said material sample holder supports said sample at a number of support points around said material sample.

15. A method for dynamically measuring viscoelasticity of material samples using shear wave induced resonance using the system claimed in claim 1, the method comprising: mounting a material sample to the rigid sample holder; providing a geometrical shape and dimensions of the material sample; selectively inducing resonance to the material sample by actuating the vibration source to apply selected shear waves to the material sample, the selected shear waves being induced to the material sample by the vibrations of the rigid sample holder; measuring the resonance of the material sample mounted to the rigid sample holder to obtain at least one of: displacement, velocity and acceleration spectra as a function of excitation frequency; and deriving the viscoelastic properties of the material sample from the measured spectra and from the geometrical shape and the dimensions of the material sample.

16. The method as claimed in claim 1, wherein said shear waves are applied vertically to said material sample holder, said measuring of the resonance of the material sample is carried out in a middle of said material sample.

17. The method as claimed in claim 1, wherein said material sample or structure is a sheet and said material sample holder comprises two plates, the material sample being sandwiched between the two plates of said material sample holder.

18. The method as claimed in claim 1, wherein said selectively inducing resonance comprises providing a transient vibration signal to said material sample holder, said measuring comprising measuring the resonance following said transient vibration signal to obtain at least one of a vibration spectrum and a vibration in time domain.

19. The method as claimed in claim 1, wherein said selectively inducing resonance comprises providing a harmonic mono-frequency or transient vibration signal to said material sample holder, said measuring comprising measuring the vibration following said harmonic mono-frequency or transient vibration signal to obtain at least one of a spectral mono-frequency vibration and a mono-frequency vibration in time domain.

20. The method as claimed in claim 1, wherein said measuring and said deriving comprise measuring at a plurality of positions on said material sample and mapping said viscoelastic properties.

21. The method as claimed in claim 1, further comprising subjecting said material sample is to a plurality of temperature conditions, and said measuring the resonance of the material sample is carried out at the plurality of temperatures.

22. The method as claimed in claim 1, wherein said viscoelastic properties are measured over time as a physical or chemical change occurs in said material sample.

23. The method as claimed in claim 1, wherein said selective inducing comprises sequential tuning of a vibration amplitude imposed on said material sample in order to reach a selected sample strain value.

24. The method as claimed in claim 1, wherein measuring the resonance of the material sample comprises measuring said viscoelastic properties several times within a time span to gather a statistical analysis of said viscoelastic properties.

25. The method as claimed in claim 1, wherein measuring the resonance of the material sample is carried out a plurality of times and the viscoelastic properties are derived from the measured resonances to measure a change in said viscoelastic properties related to fatigue of said material sample.

26. The method as claimed in claim 1, further comprising varying an amplitude of said shear waves while measuring said resonance to obtain a viscoelastic spectroscopy measurement as function of strain for the material sample.

27. The method as claimed in claim 1, wherein deriving the viscoelastic properties of the material sample is carried out by combining vibrational information at several measurement points on the material sample.

28. The method as claimed in claim 1, wherein said measuring comprises using an optical interferometer directing a point of light at an adjustable position on said material sample, and detecting a surface of said material sample.

29. The method as claimed in claim 1, further comprising introducing said material sample in an environmental chamber prior to inducing resonance to the material sample, and modifying environmental conditions in said environmental chamber while inducing resonance to the material sample; and said measuring the resonance of the material sample is carried out at different times as said material sample is subjected to the modifications of the environmental conditions, wherein modifying the environmental conditions includes at least one of modifying: humidity in the environmental chamber; ambient pressure in the environmental chamber; and immersing the material sample in an immersion fluid.

* * * * *

UNITED STATES PATENT AND TRADEMARK OFFICE
CERTIFICATE OF CORRECTION

| | | |
|---|---|---|
| PATENT NO. | : 9,494,475 B2 | Page 1 of 4 |
| APPLICATION NO. | : 13/825340 | |
| DATED | : November 15, 2016 | |
| INVENTOR(S) | : Hadj Henni et al. | |

It is certified that error appears in the above-identified patent and that said Letters Patent is hereby corrected as shown below:

In the Specification

Column 1, Line 41:
"has" should be – have –

Column 1, Line 50:
"it" should be – its –

Column 2, Line 10:
"behaviour" should be – behavior –

Column 2, Line 14:
"United-States" should be – United States –

Column 2, Line 16:
"characterisation" should be – characterization –

Column 2, Line 59:
"10 000" should be – 10,000 –

Column 2, Line 66:
After "times" insert -- faster --

Column 3, Line 23:
"characterise" should be – characterize –

Column 3, Line 29:
"of"," should be – of," –

Signed and Sealed this
Twenty-eighth Day of March, 2017

Michelle K. Lee
*Director of the United States Patent and Trademark Office*

CERTIFICATE OF CORRECTION (continued)
U.S. Pat. No. 9,494,475 B2

Column 3, Line 31:
""using","  should be – "using." –

Column 3, Line 42:
"term" should be – terms –

Column 3, Line 43:
"behaviours" should be – behaviors –

Column 3, Line 44:
"Elasticity" should be – elasticity –

Column 3, Line 46:
"behaviour" should be – behavior –

Column 5, Line 16:
"opening" should be – openings –

Column 6, Line 46:
"above described" should be – above-described –

Column 6, Line 51:
Delete "the" (2nd occurrence)

Column 7, Line 27:
"plates" should be – plate –

Column 9, Line 60:
"viscoelatsic" should be – viscoelastic –

Column 10, Line 4:
"viscoelatsic" should be – viscoelastic –

Column 10, Line 14:
"mould" should be – mold –

Column 10, Line 17:
"These" should be – This –

Column 10, Line 19:
"behaviour" should be – behavior –

Column 11, Line 64:
"moulds" should be – molds –

CERTIFICATE OF CORRECTION (continued)
U.S. Pat. No. 9,494,475 B2

Column 12, Line 6:
"mould" should be – mold –

Column 12, Line 10:
"mould" should be – mold –

Column 12, Line 17:
"mould" should be – mold –

Column 12, Line 23:
"FIG. 2 A-B, FIG. 3-A" should be – (FIG. 2 A-B, FIG. 3-A) –

Column 12, Line 25:
"FIG. 1" should be – (FIG. 1) –

Column 12, Line 51:
"positions" should be – position –

Column 13, Line 24:
"viscoelatic" should be – viscoelastic –

Column 14, Line 20:
"destabilise" should be – destabilize –

Column 14, Line 23:
"behaviour" should be – behavior –

Column 15, Line 36:
"minimise" should be – minimize –

Column 16, Line 4:
"send" should be – sent –

Column 16, Line 43:
"above mentioned" should be – above-mentioned –

Column 16, Lines 43-44:
After "interlinked" insert -- with --

Column 17, Line 13:
"utilisation" should be – utilization –

Column 17, Lines 21-22:
"dramatically" should be – dramatic –

CERTIFICATE OF CORRECTION (continued)
U.S. Pat. No. 9,494,475 B2

Column 17, Line 52:
"localise" should be – localize –

Column 17, Line 53:
"analysing" should be – analyzing –

Column 17, Lines 54-55:
"non homogeneous" should be – non-homogeneous –

Column 18, Line 40:
"above mentioned" should be – above-mentioned –

In the Claims

Column 19, Line 28, Claim 4:
"a" (2nd occurrence) should be – an –

Column 20, Line 48, Claim 21:
Delete "is"